United States Patent
Moellering et al.

(10) Patent No.: US 12,385,022 B2
(45) Date of Patent: *Aug. 12, 2025

(54) RECOMBINANT ALGAE HAVING HIGH LIPID PRODUCTIVITY

(71) Applicant: Viridos, Inc., La Jolla, CA (US)

(72) Inventors: Eric R. Moellering, San Diego, CA (US); Saheed Imam, San Diego, CA (US); Luke Peach, San Diego, CA (US); Ryan Kalb, San Diego, CA (US); Sarah Potts, San Diego, CA (US)

(73) Assignee: Viridos, Inc., La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/399,556

(22) Filed: Dec. 28, 2023

(65) Prior Publication Data

US 2024/0124858 A1    Apr. 18, 2024

Related U.S. Application Data

(63) Continuation of application No. 17/124,348, filed on Dec. 16, 2020, now Pat. No. 11,859,218.

(60) Provisional application No. 62/949,378, filed on Dec. 17, 2019.

(51) Int. Cl.
*C12N 9/16* (2006.01)
*C12N 1/12* (2006.01)
*C12N 9/10* (2006.01)
*C12P 7/649* (2022.01)

(52) U.S. Cl.
CPC ............ *C12N 9/16* (2013.01); *C12N 1/12* (2013.01); *C12N 9/1051* (2013.01); *C12P 7/649* (2013.01); *C12Y 204/01216* (2013.01); *C12Y 301/03012* (2013.01)

(58) Field of Classification Search
CPC .......... C12N 9/16; C12N 1/12; C12N 9/1051; C12P 7/649; C12Y 204/01216; C12Y 301/03012
See application file for complete search history.

(56) References Cited

U.S. PATENT DOCUMENTS

| | | | |
|---|---|---|---|
| 9,909,134 B2 | 3/2018 | Messing et al. | |
| 2013/0045323 A1* | 2/2013 | Hartel | A23L 7/10 426/627 |
| 2013/0227745 A1 | 8/2013 | Frankard et al. | |
| 2017/0152520 A1 | 6/2017 | Moellering et al. | |
| 2018/0186842 A1* | 7/2018 | Moellering | C12P 21/00 |
| 2019/0059390 A1 | 2/2019 | Djonovic et al. | |

FOREIGN PATENT DOCUMENTS

| EP | 3562833 A1 | 11/2019 |
|---|---|---|
| WO | WO 2018204798 | 11/2018 |
| WO | WO 2019/133726 A1 | 7/2019 |

OTHER PUBLICATIONS

Xue, Ya-Ping, Cheng-Hao Cao, and Yu-Guo Zheng. "Enzymatic asymmetric synthesis of chiral amino acids." Chemical Society Reviews 47.4 (2018): 1516-1561. (Year: 2018).*
Extended Search Report in European Application No. 20902766.3, dated Jun. 3, 2024, 9 pages.
Takeshita et al., "Comparison of lipid productivity of Parachlorella kessleri heavy-ion beam irradiation mutant PK4 in laboratory and 150-L mass bioreactor, identification and characterization of its genetic variation", Algal Research, Nov. 2018, 35: 416-426.
Arriola et al., "Genome Sequences of Chlorella Sorokiniana UTEX 1602 and Micractinium Conductrix SAG 241.80: Implications to Maltose Excretion by a Green Alga," The Plant Journal, 2018, vol. 93, No. 3, pp. 566-586.
Borges et al., "The Expanding World of Small RNAs in Plants," Nature Reviews Molecular Cell Biology, Dec. 2015, vol. 16, No. 12, pp. 727-741.
Chary et al., "Trehalose-6-Phosphate Synthase/Phosphatase Regulates Cell Shape and Plant Architecture in *Arabidopsis*1[W][OA]," Plant Physiology, Jan. 2008, vol. 146, pp. 97-107.
Figueroa et al., "A Tale of Two Sugars: Trehalose 6-Phosphate and Sucrose 1[Open]," Journal of Plant Physiology, Sep. 2016, vol. 172, pp. 7-27.
Hentze et al., "A Brave New World of RNA-Binding Proteins," Nature Reviews Molecular Cell Biology, May 2018, vol. 19, No. 5, pp. 327-341.
International Search Report and Written Opinion for International Application No. PCT/US2020/065323, mailed Mar. 10, 2021, 11 Pages.
Marondedze et al., "The RNA-binding Protein Repertoire of *Arabidopsis thaliana*," Scientific Reports, Published on Jul. 11, 2016, vol. 6, Article No. 29766, 13 Pages.
Okano et al., "Musashi: a Translational Regulator of Cell Fate," Journal of Cell Science, 2002, vol. 115, No. 7, pp. 1355-1359.

(Continued)

*Primary Examiner* — Robert J Yamasaki
*Assistant Examiner* — Trevor Kane
(74) *Attorney, Agent, or Firm* — DLA Piper LLP (US)

(57) ABSTRACT

The invention involves the provision of recombinant algal mutants that have a genetic modification to a nucleic acid sequence encoding a trehalose biosynthetic enzyme, and/or a genetic modification to a nucleic acid encoding an RNA binding domain And in some embodiments either of these algal mutants can further have a genetic mutation to a nucleic acid sequence encoding an SGI1 polypeptide. Attenuation of one, two, or all three of these genes results in a mutant organism with increased lipid productivity. It was also discovered that one, two, three, or more genetic mutations can be accumulated or "stacked" in a particular mutant cell or organism to result in further increases in the production of lipid products. The lipid products of these mutants are useful as biofuels or for other specialty chemical products.

12 Claims, 7 Drawing Sheets

Specification includes a Sequence Listing.

(56) References Cited

OTHER PUBLICATIONS

Ota et al., "Highly Efficient Lipid Production in the Green Alga *Parachlorella kessleri*: Draft Genome and Transcriptome Endorsed by Whole-cell 3D Ultrastructure," Biotechnology for Biofuels, Published Online on Jan. 25, 2016, vol. 9, Article No. 13, 10 Pages.

Taleb et al., "Investigation of Lipid Production by Nitrogen-Starved Parachlorella Kessleri Under Continuous Illumination and Day/Night Cycles for Biodiesel Application," Journal of Applied Phycology, 2018, vol. 30, No. 2, pp. 761-772.

\* cited by examiner

```
                         SEQUENCE LISTING

Sequence total quantity: 50
SEQ ID NO: 1           moltype = AA  length = 351
FEATURE                Location/Qualifiers
REGION                 1..351
                       note = misc_feature - RBD domain
source                 1..351
                       mol_type = protein
                       organism = unidentified
                       note = Parachlorella sp.
SEQUENCE: 1
MSSEEISKDM EEASSSGDGG GKLFLGGLSW DTTEEKLREH FGVYGDIHEA VVMKDRTTGR   60
PRGFGFVTFK DAEVADRVVQ DIHVIDGRQI DAKKSVPQEQ KPKARKIFVG GLAPETTEAD  120
FKEYFERYGS ISDVQIMQDH MTGRSRGFGF ITFEEDAAVE KVFAQGAMQE LGGKRIEIKH  180
ATPKGSSSPT TPGGRSSSGG RGQGYGRAMP MPFGQLAGSP YGYGLFHFPP GVMPHATPYS  240
MGYANPYLMM QQISGYPGAT PYPFAGLYGG QGRGASQQLQ QAQHTSQQLS SSGAGPVTRL  300
QGQQQQMPGQ GSRQQHPQAP YPRPLAGSGR GKGKVDSASE LSNHHHSAAH S           351

SEQ ID NO: 2           moltype = AA  length = 853
FEATURE                Location/Qualifiers
REGION                 1..853
                       note = misc_feature - Trehalose-6-phosphate
                       synthase/phosphatase
source                 1..853
                       mol_type = protein
                       organism = unidentified
                       note = Parachlorella sp.
SEQUENCE: 2
MGTFSRKSFS NLAALADGDF GQGSQNDLRG GGPLSLSSAA NRTSRNSIDS DGRRLQRLIF   60
VSNHLPLRVS KGATDWNFEW DDDALIAQAK EGLPEDMEAL YVGCLPVEVD PQDQDEVSLQ  120
LQKQHNCFPV FLGTELKTNY YRKFCKQQLW PILHYLIPLN PTSLGRFDPG LWASYVRANK  180
VFADKMVEVL GSLEDDFVWV HDYHLLVLPS LLRKRFHRIK CGIFLHSPFP SSEVFRTFPR  240
EEIIRSMLNA DLIGFHTFDY ARHPLSCCAR MLGLEHKTSR GAIIIEYYGR DVGIKIMPTG  300
VKPSRFLSAF SWKDTEWRRG ELAAQFKGKT VLLGMDDLDV FKGIELRLAA FKDVLEYHPE  360
```

```
WKGRLVLLQV TTTRAPGRDV DDLFDFITKQ VEEINERFGA PGYQPVVWFN RPVPMYERIA  420
MLSIADVAVV TATRDGMNLM PYEYVVCRQG PPGLAETEGP RHSQLVVSEF VGCSPSLSGA  480
IRVNPWSIEA VRDALYGAIR MPIEERHIRH EKHWKYVSSH TVQFWAKSYV TDLQRFTANH  540
SKLQCFDLGF ALDTFRMVAL TSNFRKLQTD TVVKAYQRAK KRVLLLDHDG TLMAPSSISS  600
RPTDHVLATL RQLTSDPRNT VYIISGRART ELQEWFKSVP NLGLAAEHGF YLWTPGSADW  660
AVQDPDMGFG WKEIVEPILQ VYTESTDGSH IEAKESALVW HYRDADPDFG SWQAKELLDH  720
LEGIISNEPV EIVAGQNIVE VKPQGVSKGK VVERILHDCL TASQAPEFVL CVGDDRSDED  780
MFTAMENMQF SPHMPVEVFA CTVGQKPSKA PFYVNDPAEV GGCGSRMCGG KGGEGASAPE  840
THGIGEGGGG MHL                                                    853

SEQ ID NO: 3              moltype = AA  length = 69
FEATURE                   Location/Qualifiers
REGION                    1..69
                          note = misc_feature - RNA Recognition Motif (RRM) of RNA
                           binding domain protein of SEQ ID NO: 3
REGION                    1..69
                          note = misc_feature - RNA Recognition Motif (RRM) of RNA
                           binding domain protein of SEQ ID NO: 1
source                    1..69
                          mol_type = protein
                          organism = unidentified
                          note = Parachlorella sp.
SEQUENCE: 3
LFLGGLSWDT TEEKLREHFG VYGDIHEAVV MKDRTTGRPR GFGFVTFKDA EVADRVVQDI  60
HVIDGRQID                                                         69

SEQ ID NO: 4              moltype = AA  length = 234
FEATURE                   Location/Qualifiers
REGION                    1..234
                          note = misc_feature - trehalose-6-phosphate
                           phosphatase/synthase active site domain
source                    1..234
                          mol_type = protein
                          organism = unidentified
                          note = Parachlorella sp.
SEQUENCE: 4
LLDHDGTLMA PSSISSRPTD HVLATLRQLT SDPRNTVYII SGRARTELQE WFKSVPNLGL  60
AAEHGFYLWT PGSADWAVQD PDMGFGWKEI VEPILQVYTE STDGSHIEAK ESALVWHYRD  120
ADPDFGSWQA KELLDHLEGI ISNEPVEIVA GQNIVEVKPQ GVSKGKVVER ILHDCLTASQ  180
APEFVLCVGD DRSDEDMFTA MENMQFSPHM PVEVFACTVG QKPSKAPFYV NDPA        234

SEQ ID NO: 5              moltype = AA  length = 81
FEATURE                   Location/Qualifiers
REGION                    1..81
                          note = misc_feature - trehalose-6-phosphate
                           phosphatase/synthase conserved domain
source                    1..81
                          mol_type = protein
                          organism = unidentified
                          note = Parachlorella sp.
SEQUENCE: 5
FGWKEIVEPI LQVYTESTDG SHIEAKESAL VWHYRDADPD FGSWQAKELL DHLEGIISNE  60
PVEIVAGQNI VEVKPQGVSK G                                           81

SEQ ID NO: 6              moltype = DNA  length = 4531
FEATURE                   Location/Qualifiers
misc_feature              1..4531
                          note = SGI1 gene
source                    1..4531
                          mol_type = unassigned DNA
                          organism = unidentified
                          note = Parachlorella sp.
SEQUENCE: 6
atgtctggtt cagctggatc gggccaggct actctcagac atgacggtgg ctctgctggc  60
ggcagtgggc ctgtctcaga cggttttttca ccggccggcc tgaaggtaaa gtagaaagac  120
actcatacac atcttggttc ggcgttgaaa gtaggtcatt aacatactct ataaccaata  180
tttgtaggtt ctggtcgtgg acgacgacct catgtgcctt aaggtggtgt cagccatgtt  240
gaaagaggtgc agctatcaag gtgaggtctt tactggtgtc tgttattgct gtaacatcat  300
ttcgctgttg cacaatttaa acatttgtaa tttactgttg ttattgcagt ggccacttgt  360
agcagtggca gcgaggcact gacacttcta cgtgaacgca acgaggacgg atcctccgac  420
cagttcgacc tcgtactgtc agatgtttac atgccgggta tgtcgtattc ctttgtaaac  480
tttacaatat gcgtcagtt tgacgcgtac actttgtaca ctttgcaaaa acgcaccctg  540
cgaggtctgc catttggtca ctacaacttg gccaccttgg ttgcaagttt gcaagttcgc  600
tctacgtcaa cgctgcaaaa tgaaccaatt gttttgcact gacccgtgcca accttcattt  660
gtggctgcag acatggacgg tttcaagctg cttaacaca tcggtctaga gttggagctt  720
cccgttatca gtaagttgat cgagccgagt ccagagcgaa gctgcttct atactattag  780
cagctgtctt tgatatttg acagcttgac ttgatatggt cacagagcat acttgcaacc  840
aggttacctt tgaactagc aactgtgccc aagcatctct tcaagcacct ccgtcagtcc  900
atagggtact gttgatttgt actctgcaat actgcactgt aatgcgctgt gaatcactgc  960
```

```
ccttcacctc tagatggtgc ttccctggag ccctccccca cctccgcctc aagcccctca  1020
catgcctctc ccccccctgc agtgatgtca tccaacgggg acacgaatgt cgtgctgcgg  1080
ggggtcaccc acggggctgt ggactttctg atcaagcccg ttcgaattga ggagctgcgg  1140
aacgtgtggc agcacgtggt gcgtcgtcgt tccatggcgc tggccaggac gccagacgag  1200
ggggacact cggacgagga ctctcaggtg cccttgacga cttctggcg gcttgctgtg  1260
tcggatgcca cttggactgg ggatgcacga ggggtggggg gacaatggga gatgggccat  1320
agtaggccag agttgatggc agtggtggtg gggggagta ggcggagag aagcagccat  1380
cctggtgttg gttttgatga ttgagtgcat ggggatgatg cacaggtgag ctgactggat  1440
gccttgtctt gctgtgctgc gctgcagcgg cacagtgtga aacgcaagga gtcggagcag  1500
agcccgctgc agctcagcac agagcagggc gggaacaaga agccaagagt ggtgtggtcg  1560
gtggagatgc accaacaggt gtgcttgcgg gcgggtgtat acggggagg ggggccagct  1620
gctggctgac ctggcgtgcg cggtgcattg cacttggcga tgagggggcgt gcttcagtat  1680
gtagctggga cgcaattggt tgtgctgtgt gaccagtgca caaatacat ccctgaattc  1740
cagtgggttg aacagagttg tcctggaggt gggaagcaaa cgcgcacgtg gtagaggggga  1800
gcagggtgca gaacagccgc agcagggggt ttgcgcagtg tgcaggtatc ctgcctccat  1860
gccccgggcc atgggcatac tacgctggta ccgtcaggat gggcgttgag cctggcttgg  1920
ggggcagggg gcgagcgaat gcggaatggg agcggcaggt gctgggaggg tggctgactg  1980
gcttgcagga gcgcaagtcc tgtcgggggc gtcgtcctgt tccctcctgc ccgcttcacc  2040
cacgttcact ctcatgcctc cacactcctg ctgctgacac acctgtcgcc acctccgctg  2100
cagtttgtga acgcggtcaa ctccctgggc attgacaagg cggtgcccaa gcggattctg  2160
gacctgatga acgtggaggg gctgacgcgc gagaacgtgg ccagccatct gcaggtgcct  2220
gccatgaccc ctcccaccag ggacctggtg ttttgacacc ctggaactcc tctttgacag  2280
agcctccagt tcaattccag caatcgaatt gaatcaaaaa gcatgtgcac ccacgtgctg  2340
tttgaatgtc ccatgtggta ggaaacacaa ctgccccctt gccatttgct ggagggtgcc  2400
cgctgcgcca tgcccgagtg cgctgtgctc agcgttgtgc tgcgccccc gctgactgaa  2460
gctgacgcg tgcggctgag gaggtactg ggggagggg ggtgggaggc ggccgctggc  2520
ggcgaaggg agggtgtgca cgcatggaca cagggccttt ccgccctgca cggcctctac  2580
tgcaccctgc cacgtgatgt atcgacatgg tgggccatgc tgtgctgtgc cgctgcagaa  2640
gtaccgcctg tacctgaagc gggtggaggg agtgcaatcg ggtgcggcag cctccaagca  2700
gcaccagcac ccgcagtatc aaccagcagca gcagcagcac caagcgcaac ctcgtgcagc  2760
tgtctcccct gcagcagctt cctttggtgc cctttccttg ggagccccgc agcaggcgca  2820
gcagggcatg ccgcagctgg ggatgcctgt gcaggtgaag actgcccccc ccccctccc  2880
cctttccatc ttccctccat cagcctgctg ttccttaccc ttgtcaaccc gtctctcctt  2940
tttcgcaagc agcgcaccac ccccatgca cgccttgcct ggcactgttg tcagctgccc  3000
ccctagaaat acacaaggtg tgggtgcaac tggtgggacc ccctccccc ccccccctgg  3060
gctgcagggt ctccctccaa acttggcagc catgggatcc cagccgccgc acatcccctt  3120
ccagcaggcc ctggccatgc aggcggcggc tgcggcggct gcagcagcg gcgcgctccc  3180
cgggagtctg ccccccctaca tgccacccc ggggatgatg ccccccggca tgccgggggg  3240
ggtccccggt atggggggg tggtgggca tcctcaggta gggcagcac atgagtgggc  3300
aggggtattg gagaggggaa gggcaggag gttgcatgtg aggggctgca tggcaaagag  3360
gctgcagcgc aggtgttgct tgcagcactt ccctcggtg gcgcttgcat caaatttga  3420
atcctccccc gatgggcacg cccgtgtgtg ggggggggtg ggatggggga tggggtggt  3480
tttgtggcat gtcgggcgct ttcatctacc cgggccccg ccctgcctg tacgcgtgcg  3540
catgtgtgca gatgcccgcc ccagggatgg actttgcggg tttcaacggg tatggcaacg  3600
ctgcggggggg gctgatgttt ggcgggcagc agcaggcgca gcacgcgcag cagcacgcgt  3660
cagcgcaagc gggctcgctg gcgcagcagc aggcgcagca agtatccatg ggcttgggcc  3720
ttatgcccc ccgttgggg ttccccca cctcgctcgc cgcgccagcc cgcggctccg  3780
cagcaactga gcccgccgca gccccactcc ccctgacgtc ctcgccgcca gctgcttcag  3840
caggcggcag cggcggccca gcagcagctg ctccgcagca cagcagcggc gccgcagcag  3900
cccaagcccc ccatcaccac ccacagtgct cggagcaggg agcgggggg ctcccgcccc  3960
cgctgcccgc gtccagcgcc ccgcagtcct atccccctcc tcccccctcc tcgcaggccg  4020
ctttgcatga cccggacgaa cactaccccc caggctcggc agaggtgagc acgtcccccc  4080
gccccctccc ccccccccc cccccttccc ttcaccctgg cttggcgtgc aatgaaaccc  4140
taaataaccc taaaacctca ttatcagttg caaattggac ccgtgaagcg ggcggggggca  4200
actgcgctct gctggtgtca gcgctgtctc tgccggttcc tgcccagcgt gcgcctgcat  4260
gcaagggggg atgggggggg ggaggcattt aacaataggc cagtcatctc caatccaccg  4320
tcaatttcag ccccctcccc cccctccct catccccttg cagatgcacc accagcacct  4380
cccagggctg tgtggcttta acccggacga cctgctgggg gggcagctgg gggacatggg  4440
gttcctgggg gagctggggg gggcggtggg aggaaagcac gaacaggacg acttcctgga  4500
cctgctgctg aaggggagg aggagctgtg a                                 4531
```

SEQ ID NO: 7        moltype = DNA  length = 1860
FEATURE               Location/Qualifiers
misc_feature       1..1860
                      note = SGI1 gene coding sequence
source                1..1860
                      mol_type = unassigned DNA
                      organism = unidentified
                      note = Parachlorella sp.
SEQUENCE: 7

```
atgtctggtt cagctggatc gggccaggct actctcagac atgacggtgg ctctgctggc   60
ggcagtgggc ctgtctcaga cggttttca ccggccggcc tgaaggttct ggtcgtggac  120
gacgacctca tgtgccttaa ggtggtgtca gccatgttga agaggtgcag ctatcaagtg  180
gccacttgta gcagtggcag cgaggcactg acacttctac gtgaacgcaa cgaggacgga  240
tcctccgacc agttcgacct cgtactgtca gatgtttaca tgccggacat ggacggtttc  300
aagctgcttg aacacatcgg tctagagttg gagcttcccg ttatcatgat gtcatccaac  360
ggggacacga atgtcgtgct gcgggggtc acccacgggg ctgtggactt ctgatcaag  420
cccgttcgaa ttgaggagct gcggaacgtg tggcagcacg tggtgcgtcg tcgttccatg  480
gcgctggcca ggacgccaga cgagggggga cactcggacg aggactctca gcggcacagt  540
```

-continued

```
gtgaaacgca aggagtcgga gcagagcccg ctgcagctca gcacagagca gggcgggaac   600
aagaagccaa gagtggtgtg gtcggtggag atgcaccaac agtttgtgaa cgcggtcaac   660
tccctgggca ttgacaaggc ggtgcccaag cggattctgg acctgatgaa cgtggagggg   720
ctgacgcgcg agaacgtggc cagccatctg cagaagtacc gcctgtacct gaagcgggtg   780
gagggagtgc aatcgggtgc ggcagcctcc aagcagcaac agcaccccgca gtatcaccag   840
cagcagcagc agcagcaagc gcaacctcgt gcagctgtct cccctgcagc agcttccttt   900
ggtgcccttt ccttgggagc cccgcagcag gcgcagcagg gcatgccgca gctggggatg   960
cctgtgcagg gtctccctcc aaacttggca gccatgggat cccagccgcc gcacatcccc  1020
ttccagcagg ccctggccat gcaggcggcg gctgcggcgg ctgcagccag cggcgcgctc  1080
cccggggagtc tgccccccta catgccaccc cggggatga tgcccccgg catgccgggg  1140
ggggtccccg gtatgggagg ggtggtgggg catcctcaga tgcccgcccc agggatggac  1200
tttgcgggtt tcaacgggta tggcaacgct gcggggggc tgatgtttgg cgggcagcag  1260
caggcgcagc acgcgcagca gcacgcgtca gcgcaagcgg gctcgctggc gcagcagcac  1320
gcgcagcaag tatccatggg cttgggcctt atgcccccgc cgttgggggtt cccgcccacc  1380
tcgctcgccg cgccagcccc gcgctccgca gcaactgagc cgccgcagc cccactcccc  1440
ctgacgtcct cgccgccagc tgcttcagca ggcggcagcg gcggcccagc agcagctgct  1500
ccgcagcaca gcagcggcgc cgcagcagcc aagcccccc atcaccaccc acagtgctcg  1560
gagcaggag cggggggct cccgccccg ctgcccgcct ccagcgcccc gcagtcctat  1620
cccctccctc ccccctcctc gcaggccgct ttgcatgacc cggacgaaca ctacccccca  1680
ggctcggcag agatgcacca ccagcacctc ccagggctgt gtggctttaa cccggacgac  1740
ctgctggggg ggcagctggg ggacatgggg ttcctggggg agctgggggg ggcggtggga  1800
ggaaagcacg aacaggacga cttcctggac ctgctgctga ggggggagga ggagctgtga  1860
```

```
SEQ ID NO: 8                moltype = AA  length = 619
FEATURE                     Location/Qualifiers
REGION                      1..619
                            note = misc_feature - SGI1 polypeptide
source                      1..619
                            mol_type = protein
                            organism = unidentified
                            note = Parachlorella sp.
SEQUENCE: 8
MSGSAGSGQA TLRHDGGSAG GSGPVSDGFS PAGLKVLVVD DDLMCLKVVS AMLKRCSYQV    60
ATCSSGSEAL TLLRERNEDG SSDQFDLVLS DVYMPDMDGF KLLEHIGLEL ELPVIMMSSN   120
GDTNVVLRGV THGAVDFLIK PVRIEELRNV WQHVVRRRSM ALARTPDEGG HSDEDSQRHS   180
VKRKESEQSP LQLSTEQGGN KKPRVVWSVE MHQQFVNAVN SLGIDKAVPK RILDLMNVEG   240
LTRENVASHL QKYRLYLKRV EGVQSGAAAS KQHQHPQYHQ QQQQQQAQPR AAVSPAAASF   300
GALSLGAPQQ AQQGMPQLGM PVQGLPPNLA AMGSQPPHIP FQQALAMQAA AAAAASGAL   360
PGSLPPYMPP PGMMPPGMPG GVPGMGGVVG HPQMPAPGMD FAGFNGYGNA AGGLMFGGQQ   420
QAQHAQQHAS AQAGSLAQQQ AQQVSMGLGL MPPPLGFPPT SLAAPAPRSA ATEPAAAPLP   480
LTSSPPAASA GGSGGPAAAA PQHSSGAAAA QAPHHHPQCS EQGAGGLPPP LPASSAPQSY   540
PLPPPSSQAA LHDPDEHYPP GSAEMHHQHL PGLCGFNPDD LLGGQLGDMG FLGELGGAVG   600
GKHEQDDFLD LLLKGEEEL                                                619
```

```
SEQ ID NO: 9                moltype = AA  length = 302
FEATURE                     Location/Qualifiers
REGION                      1..302
                            note = misc_feature - SGI1 polypeptide, NCBI Accession
                             XP_005652114
source                      1..302
                            mol_type = protein
                            organism = unidentified
                            note = Coccomyxa subellipsoidea
SEQUENCE: 9
MGLKARAASV SVHSSANNTA SPLSSGRRGF PHSGEMSGED LARSDSWEMF PAGLKVLVVD    60
DDPLCLKVVE HMLRRCNYQV TTCPNGKAAL EKLRDRSVHF DLVLSDVYMP DMDGFKLLEH   120
IGLELDLPVI MMSSNGETNV VLRGVTHGAV DFLIKPVRVE ELRNVWQHVV RRKRDQAVSQ   180
ARDSRDISDE EGTDDGKPRD KKRKEVILVL WWDMQRRDSD DGVSAKKARV VWSVEMHQQF   240
VQQAVNQLGID KAVPKRILDL MNVDGLTREN VASHLQVPHL SIFSPLFAEL MSTLPRRCFY   300
DF                                                                  302
```

```
SEQ ID NO: 10               moltype = AA  length = 270
FEATURE                     Location/Qualifiers
REGION                      1..270
                            note = misc_feature - SGI1 polypeptide, NCBI Accession
                             XP_001415508
source                      1..270
                            mol_type = protein
                            organism = unidentified
                            note = Ostreococcus lucimarinus
SEQUENCE: 10
FPAGLGVLVV DDDLLCLKVV EKMLKACKYK VTACSTAKTA LEILRTRKEE FDIVLSDVHM    60
PDMDGFKLLE IIQFELALPV LMMSANSDSS VVLRGIIHGA VDYLLKPVRI EELRNIWQHV   120
VRRDYSSAKS SGSEDVEASS PSKRAKTSGS NSKSEEVDRT ASEMSSGKAR KKPTGKKGGK   180
SVKEAEKKDV VDNSNSKKPR VVWSAELHAQ FVTAVNQLGI DKAVPKRILD LMGVQGLTRE   240
NVASHLQKYR LYLKRLQGND ARGGGNASST                                    270
```

```
SEQ ID NO: 11               moltype = AA  length = 941
FEATURE                     Location/Qualifiers
```

| | | |
|---|---|---|
| REGION | 1..941 | |
| | note = misc_feature - SGI1 polypeptide | |
| source | 1..941 | |
| | mol_type = protein | |
| | organism = Chlamydomonas reinhardtii | |
| SEQUENCE: 11 | | |

```
MDSQGVKLEE HPGHTGGHWQ GFPAGLRLLV VDDDPLCLKV VEQMLRKCSY EVTVCSNATT    60
ALNILRDKNT EYDLVLSDVY MPDMDGFRLL ELVGLEMDLP VIMMSSNGDT SNVLRGVTHG   120
ACDYLIKPVR LEELRNLWQH VVRRRRQHAQ EIDSDEQSQE RDEDQTRNKR KADAAGVTGD   180
QCRLNGSGSG GAAGPGSGGG AGGMTDEMLM MSGGENGSNK KARVVWSVEM HQQFVNAVNQ   240
LGIDKAVPKK ILEIMGVDGS AGRLADTSGR DVCGTVYRLY LKRVSGVTPS GHHHNAAHKS   300
NKPSPHTTPP PPALPGQAGT HPANQATAIP PPPQPGSGTA AGAGAAAAGT GGGAAAANGH   360
AATTGAGTPG AAPGAGGGVG GTGAGGLGSG PDGAAAAAGP GPGAAVPGGL GGLPLPPGAG   420
PGPGPGGFGG PSPPPPPHPA ALLANPMAAA VAGLNQSLLN AMGSLGVGVG GMSPLGPVGP   480
LGPLGGLPGL PGMQPPPLGM GGLQPGMGPL GPLGLPGMGG LPGLPGMNPM ANLMQGMAAG   540
MAAANQMNGM GGHMGGHMGG MNGPMGALAG MNGLNGAMMG GLPGMGGPQN MFQAAAAAAA   600
QQQQQQQEQQ HAMMQQAAAG LLASQQQQQQ QQQQQQQQQA LQQQQQQGMA VSPPGPHNAT   660
PNGQLHTHPQ AHHHPHQHLN AHAHPHQHLN TAPAGALGLS PPQPPAGLLS ASGLSSGPDG   720
SGLGSGVGGL LDGLQQHPHH PQLQLAGSLG TGGTGRSSGA AGRGSLDLPA DLMGMALLDF   780
PPVPVPGGAD VGMAGAGGGA AGAHHHGHQG HQGIGGGAGV GIAGGVGCGV PAAAHGLEPA   840
ILMDDPADLG AVFSDVMYGT PGGGGVPGGV PGGGVGLGLG AGQVPSGPAG AGGLHSHHHQ   900
HHHHQHHLGH VVPVGGVDPL AGDAAKMAMN DDDFFNFLLK N                      941
```

| | | |
|---|---|---|
| SEQ ID NO: 12 | moltype = AA  length = 523 | |
| FEATURE | Location/Qualifiers | |
| REGION | 1..523 | |
| | note = misc_feature - SGI1 polypeptide | |
| source | 1..523 | |
| | mol_type = protein | |
| | organism = unidentified | |
| | note = Chromochloris zofingiensis | |
| SEQUENCE: 12 | | |

```
MDGFKLLETV GLELDLPVIM MSSNGEHTTV MRGVTHGACD FLIKPVRIEE LRNIWQHVIR    60
RTRHPVFRDL EPDDHEGGDY EASKKRKDLY RGENSSGSGG AGGLERDDDG SASKKPRVVW   120
SVEMHQQFVQ AVNQLGIDKA VPKKILELMN VDGLTRENVA SHLQKYRLYL KRVQGVQAPF   180
GLPNIQLPRQ TSSKGAGSSS QQQHHQQQQH QQQHQHQHQT ALGTGQQQSH QLQPCPVSTA   240
TPVMPSPDAM VAASMMSSQA MAAMAPGVMN PMTAMNSMMA GLNPNMMGMA AGLGLAGLGI   300
GGMAGHPVPN PMLAGMGPMG LGLPPPPGMP PPPPGMPPGM PPGMPPGMPA MMQGLSMAGM   360
SHLAAAGMRP PPGALGGHLG GPGLSPFGPP PPPGADPANM MANMSSMMAN MQAALAFQAD   420
AAAAAQHQAA STGSVAPGRQ QQVHQHQQAV GMAVDDAAAF PSPGCRPNGS ADAGAQSAAE   480
PNDFSRVFDD PFAQPAASPS GAAAAGSNEA PGMDDFLDFF LKS                    523
```

| | | |
|---|---|---|
| SEQ ID NO: 13 | moltype = AA  length = 832 | |
| FEATURE | Location/Qualifiers | |
| REGION | 1..832 | |
| | note = misc_feature - SGI1 polypeptide | |
| source | 1..832 | |
| | mol_type = protein | |
| | organism = unidentified | |
| | note = Volvox carteri | |
| SEQUENCE: 13 | | |

```
MDGRAEGTVA IKQEDHASGH WHNFPAGLRL LVVDDDPLCL KVVEQMLRKC SYDVTTCTNA    60
TMALNLLRDK STEYDLVLSD VYMPDMDGFK LLEVVGLEMD LPVIMMSSNG DTSNVLRGVT   120
HGACDYLIKP VRLEELRNLW QHVVRRRRQL NLDMDSDEHS QERDDDQGRK RKADTAGCIG   180
DQLRMMGAGC SGGANGLGST GNLGAVATGS AGLGLGLGDN ADELGLGLDN GSSKKARVVW   240
SVEMHQQFVN AVNQLGIDKA VPKKILEIMN VDGLTRENVA SHLQKYRLYL KRVSGAQQPG   300
QNRVSRPSPP QPQSPQVPSQ QQQSLPGGGG AAAAGAGQLQ GGGGAAAAAA SLASILAGGG   360
PAGGGAGAGP PPGGGQLGAD GGGPGPGLSS AVANAMSAAA AAGGFPTPPP PPPPHPAALL   420
AANPMMAAAA GLNPLLGAMG GLGVGPLGPL NPLNGMPMPG MQPPLGLLPG LPGPGGQLGL   480
GPLGPIGLPG PGPLPSLPAG LPLNPMANGL QQMAAANLMQ GMAGMGQLPA LSMNGMNGIM   540
GPLPGVGLPG PQQHLFPQQQ QPHLQQQQQQ QQQKDLQMAQ KQHQAAAAAA AVAAAVAAAQ   600
HQQQQPQAQQ QPQPQQQQQQ PGKLPQATVG TPALASPAGA LPRQPSGQHP HTLSSSSLHT   660
QQPHQQQLLH SQPSSTHLAT NNTLAMAPAL NGTLDVGKKG HLHAAGGQGA GAGAGAVLDI   720
PPDLIGGLIE DGFGAPPGPT IQLAHGTAAV LDPTMLLDEG DNSDFAAVFQ EMSSYGGGGV   780
IGGGGSGAGA MGVLGHGLLA AGGPVMVDVA AGLAGVTETA TRVDDDFLNF LL          832
```

| | | |
|---|---|---|
| SEQ ID NO: 14 | moltype = AA  length = 446 | |
| FEATURE | Location/Qualifiers | |
| REGION | 1..446 | |
| | note = misc_feature - SGI1 polypeptide 5172 | |
| source | 1..446 | |
| | mol_type = protein | |
| | organism = Tetraselmis sp. | |
| SEQUENCE: 14 | | |

```
MSCTVASFPP AAGGQGSPAT PVPYQDLLVK RQDQWSNFPA GLRVLVADND PASLQQVEKM    60
LKKCSYQVTL CSSGKNSLEI LRKRREEFDL VLADANLPDI DGFKLLHVCH TELSLPVVLM   120
SGTSDTQLVM RGVMDGARDF LIKPLRVEEL KVLWQHLVRF TSEITKTDAQ LNVVKVELDG   180
GRPAGEVSTS QNGSQCTERE GEGNSSKKQR MNWSDEMHQQ FVNAVNQLGI DKAVPKRILD   240
LMSVEGLTRE NVASHLQKYR IYLKRMANHQ ENGKQAVMST DTIARAEEAY QGGMPQGGQM   300
```

```
MQQEHSGQAV QYSQPHAPGG LHQQAMPAQM HMGMMPAGPQ PGSMQMAPHH VMQMPNGQVM   360
VMQQMGPRPG MPPGMPQQMM ASSQQMGMLQ PGMPAGQMLH FQHPQQVHQH PPSSGPMHAV   420
QHMEYAYSQP MQMAGWPVQG QPGNQA                                        446

SEQ ID NO: 15           moltype = AA   length = 490
FEATURE                 Location/Qualifiers
REGION                  1..490
                        note = misc_feature - SGI1 polypeptide 5185
source                  1..490
                        mol_type = protein
                        organism = Tetraselmis sp.
SEQUENCE: 15
MTPTPPMSCT VASFPPAAGG QGSPATPVPY QDLLVKRQDQ WSNFPAGLRV LVADNDPASL    60
QQVEKMLKKC SYQVTLCSSG KNSLEILRKR REEFDLVLAD ANLPDIDGFK LLHVCHTELS   120
LPVVLMSGTS DTQLVMRGVM DGARDFLIKP LRVEELKVLW QHLVRFTSEI TKTDAQLNVV   180
KVELDGGRPA GEVSTSQNGS QCTEREGEGN SSKKQRMNWS DEMHQQFVNA VNQLGIDKAV   240
PKRILDLMSV EGLTRENVAS HLQKYRIYLK RMANHQENGK QAVMSTDTIA RAEAAYQGGM   300
PQGGQMMQQE HSGQAVQYSQ PHAPGGLHQQ AMPAQMHMGM MPAGPQPGSM QMAPHHVMQM   360
PNGQVMMQQ MGPRPGMPPG MPQQMMASSQ QMGMLQPGMP AGQMLHFQHP QQVHQHPPSS   420
GPMHAGGEMI DPGSMQRLHQ QPHYIGPNGQ HMPAPAMGMP SGTVQHMEYA YSQPMQMAGW   480
PVQGQPGNQA                                                          490

SEQ ID NO: 16           moltype = AA   length = 574
FEATURE                 Location/Qualifiers
REGION                  1..574
                        note = misc_feature - SGI1 polypeptide 5230
source                  1..574
                        mol_type = protein
                        organism = Tetraselmis sp.
SEQUENCE: 16
MTMPLGGGLC MKDRIHGDER YRSKAKRQVN TIFAFTQRNT WRGRFRLCSY RTTELLGGSK    60
TTEPGRGTFV LQIFMCVKNA SIDDGSRHIS TSRGLESVLK RRGGQGAPAA PVPYHDLLVK   120
RQDQWSNFPA GLRVLVADND PASLQQVEKM LKKCSYQVTL CSSGKNSLEI LRKRREEFDL   180
VLADANLPDI DGFKLLHVCH TELSLPVVLM SGTSDTQLVM RGVMDGARDF LIKPLRVEEL   240
KVLWQHLVRF TSEITKTDAQ LNVVKVELDS GRPAGEVSTS QNGSQCAERE GEGNSSKKQR   300
MNWSDEMHQQ FVNAVNQLGI DKAVPKRILD LMSVEGLTRE NVASHLQKYR IYLKRMANHQ   360
ENGKQAVMST DTIARAEAAY QGGMPQGGQM MQQEHSGQAV QYSQPHAPSG LHQQAMPAQM   420
HMGMMPAGPQ PGSMQMAPHH VMQMPNGQVM VMQQMGPRPG MPPGMPQQMM ASSQQMGMLQ   480
PGMPAGQMLH FQHPQQVHQH PPSSGPMHAG GEMIDPGSMQ RLHQQPHYIV PNAQHMPAPA   540
MGMPPGAVQH MEYAYSQPMQ MAGWPVQGQP GSQA                               574

SEQ ID NO: 17           moltype = AA   length = 674
FEATURE                 Location/Qualifiers
REGION                  1..674
                        note = misc_feature - SGI1 polypeptide 5549
source                  1..674
                        mol_type = protein
                        organism = Oocystis sp.
SEQUENCE: 17
MLAFTHQRMT TAPALAVATS HFFAHVRVTT GSSAIATVFA ARSRGSGLLA GFNTMENVKV    60
EVPEVVPENV NFPAGLKVLV VDDDPLCLKV IDQMLRRCNY AATTCQSSLE ALELLRSSKE   120
NHFDLVLSDV YMPDMDGFKL LEIIGLEMGL PVIMMSSNGE TGVVFRGVTH GAVDFLIKPV   180
RIEELRNLWQ HVVRKTMVVP SNDKATSEED GEESKHRVDR KRKESFHSRA REQVEIACSV   240
VPALLWPTVP PSSVHPTSSS FLRSHVLLLQ RSSGGKDVLD EGGSNAKKPR VVWSVEMHQQ   300
FVNAVNQLGI DKAVPKRILD LMNVDGLTRE NVASHLQKYR LYLKRVAGIN TATGSRNGKG   360
RSDVSGLSGM PNGSLPMPGM MPPHMAAGML LAGMAADVGP RPHPFPIMPM PAMALQGMHG   420
GMAQMMQLPP GMPPPMMMPM APLLPSQLAA LGQQQQQQQQ QQVARSESMP SENGVAGPSG   480
SFTAMLNGPA PMESSPFAAL QVFGPPQGME QLTQQQQQQQ QAGAAAFVAA FAAANGGDMQ   540
GGGGGPGPML GGAGGAGPLL GGVGGGDPLH GGGGSSALGG RPMMSAEQPM GGSGGLASNS   600
LTVQQNDLAQ MCSQLDVNGL QAVAAAAAAG AMGAPGGAGG AMPPSSVGGV GPDMKLTEQD   660
DFFSFLLKDS NLID                                                    674

SEQ ID NO: 18           moltype = AA   length = 488
FEATURE                 Location/Qualifiers
REGION                  1..488
                        note = misc_feature - RCC299, SGI1 polypeptide
source                  1..488
                        mol_type = protein
                        organism = Micromonas sp.
SEQUENCE: 18
MSTPAVSKGF PIGLRVLVVD DDPLCLKIVE KMLKRCQYEV TTFSRGAEAL KTLRERKDDF    60
DIVLSDVHMP DMDGFKLLEH IALELDIPVM MMSANCATDV VLRGIIHGAV DYLLKPVRIE   120
ELRNIWQHVV RRKRESSQGN LRSGEGGSNG RTVSGGSTGE GGGKDSKGSS EQHGDAKDKT   180
GSAGGSGGSS KRKKGSGGKK DEGTDEVKDG SGGDENEDSS ALKKPRVVWS AELHQQFVTA   240
VNQLGIDKAV PKRILDLMGV QGLTRENVAS HLQKYRLYLK RLQGVNSGGA PGGGPGFMSP   300
IALDGSMVQG GPGGRVGSPA IGGPNGPIMV GHGHIDAPML AGGAPQTIQM GMVYGGPGMG   360
PPQMMAPNGK GGGGMPGGYV MQPGMMMAPN GQMMPVGQMG PGGMMVQGPG GGMMQMHDGG   420
MMNGNGSYGS LQNMKQGNGV VMMPNGGMGG VDGAIPNMAT GLINGQGLPD DDVLDMFLKD   480
GLPEGEGF                                                            488
```

```
SEQ ID NO: 19            moltype = AA  length = 544
FEATURE                  Location/Qualifiers
REGION                   1..544
                         note = misc_feature - SGI1 polypeptide
source                   1..544
                         mol_type = protein
                         organism = Micromonas pusilla
SEQUENCE: 19
MTAEKKELKV FPAGLRVLVV DDDPLCLRIV EKMLKRCQYE VTTFSRGAEA LETLRARRDD    60
FDIVLSDVHM PDMDGFKLLE HIALELDVPV MMMSANCATD VVLRGIIHGA VDYLLKPVRL   120
EELRNIWQHV VRRQREPSKD GAAGKGGGAS GAPEVSGDTH ANTDDKQDGN ATDSKGSGSQ   180
KRKSGKSGDD GGKDGGGSGG KDGDASNKGN NNKRKKGKSN DATETAGGAG VEDNDDTSGL   240
KKPRVVWSPE LHQQFVTAVN QLGIDKAVPK RILDLMGVQG LTRENVASHL QKYRLYLKRL   300
QGVNNNGTVP SGAAGFMTGL AIDGVGGVMG PPTTGSPAMN GPGGPGGGLV MGPGHMGGPH   360
MDGSGMMHMG PGGPMAGMTV VYGGGMPGGM PGGADSKNGA SGQPPPGGYV VMGGPHGGGP   420
GGAPMMMQHG GMVPGPGPGL VPGPGGSLMM PAGMMPDGGG GMVGVHVPGG VVMGQHQLGG   480
KHSSGGAGMA GGSAAGKGAQ RGGVGGAFDV PPTNGSLDAD EIGDDVLTMF LKDGLPEMND   540
GDAL                                                                544

SEQ ID NO: 20            moltype = AA  length = 776
FEATURE                  Location/Qualifiers
REGION                   1..776
                         note = misc_feature - SGI1 polypeptide
source                   1..776
                         mol_type = protein
                         organism = Sphagnum fallax
SEQUENCE: 20
MSGGDLSRVR EGTADLDPVM ASHQHPPPRQ QSHQQPKNHQ QEAHQQHCSS AETTSPNNTA    60
RGAGATYGKM EPADDFPPAGL RILVVDDDPT CLAILKKMLQ QCSYQVTTCG RATRALELLR   120
EDKDKFDLVI SDVYMPDMDG FKLLELVGLE MDLPVIMMSG NGETSVVMKG ITHGACDYLL   180
KPVRIEELSN IWQHVVRKLR SEPKEHSASL EDGDRQRRGG AEDADNTSSA ADTADGIWRN   240
KKKKEAKEDE EDFEQDNDDP STLKKPRVVW SVELHQQFVS AVNQLGIDKA VPKRILELMS   300
VQGLTRENVA SHLQKYRLYL KRLSGVTSQS NSLNVSFGGP DAGYGGLFGL DEMSDYRNLV   360
TNGHLPAQTI AALHHANMAG RLGASSGMVG PSSPLDPSVL AQIAALQSGS LPRPGMDGSL   420
QGNQAGLLQS LSGALDYNSL HQSHLLPAIG QLGQLDELPS LKSMQHQLGM GSLGGSTRNL   480
AGSPNEELTM QLLQQQRAQQQ SGGSPINLPQ ATGILRPLSS NINQGGSVPN LVGVIPGTAI   540
GLSNMCSGGR EFGSSSGLLS ASGSLMQSST VEAQNLNFGG SSGSSGCSFQ ASVLSSKTGG   600
LEDLNPAKRV RTTYSALSHS SPDLGQSSRP AWLGSQEGLV HGDPVYSPHQ LSLSPRQDIVG   660
GIGSSGRPAY MGSQSMGSLG MNFPLSLAVD AGAVRPSLTR GQSLTEQVAA NRELKFPKEE   720
RGRDNLMCAR LGGGMITNES SSEELLNYLK QSHEGLGFME GDLVSDGYPV DNLYVK        776

SEQ ID NO: 21            moltype = AA  length = 715
FEATURE                  Location/Qualifiers
REGION                   1..715
                         note = misc_feature - SGI1 polypeptid
source                   1..715
                         mol_type = protein
                         organism = Physcomitrella patens
SEQUENCE: 21
MGGGYLSSTV NMGESRDGGS PAMATLQQQQ KHQPLNPNHQ NPRNRSNSSP TNCYSNTAWG    60
AKPAKLDTPD EFPVGMRVLV VDDDNPTCLMI LEQMLVRCAY RVTTCGKATE ALSMLREDIG   120
KFDVVISDVD MPDMDGFKLL ELVGLEMDLP VIMVSGNGET SAVMKGITHG ACDYLLKPVR   180
IEELRNIWQH VVRKKRREVK AVATKSVEEA GGCERPKRGG GADDADYTSS ATDTTDSNWK   240
LTKRRKGEFK DENEEDNEQE NDDPSTLKRP RVVWSVELHQ QFVSAVNQLG IDKAVPKRIL   300
ELMGVQGLTR ENVASHLQKY RLYLKRLSGV TSQQGNMSAH FGGSDPFCMM PPDMSLANGQ   360
LTPQALAKFH MLGRMNATNG IGFSGGGLDP GMNQMFLQDL PRPPQLNSML RNNTGLLASV   420
PNGLQHLEQL SEPHHVHVVN ELEHYPSNTK VYPQLNGNLD VSVGPLGAAN GNLASNPNSD   480
TLLMHILHSR ASQQGVGSPS TLPQPRCGLN PTHLLSNDIN FAPVGSLPNL AGSLGPAVGL   540
SAIPGSAGGR DLSPSVGGSG ASLSSPLGSL VRRPLMAEEQ SNPVNSTNGT YSMAHSGQSP   600
KPSGDTLPTP LNEGLEQQQP LWALYQNPMN QLSHGPSQGF PHDSLQWSVL TENLSFGDMG   660
QSLSAGLISQ FSSQGQDNGI GFAPPSQRGS YTRQSVSFPA SSALDGRMVR SSYEP         715

SEQ ID NO: 22            moltype = AA  length = 60
FEATURE                  Location/Qualifiers
REGION                   1..60
                         note = misc_feature - Myb domain of SGI1 polypeptide of SEQ
                         ID NO: 8
source                   1..60
                         mol_type = protein
                         organism = unidentified
                         note = Parachlorella sp.
SEQUENCE: 22
KKPRVVWSVE MHQQFVNAVN SLGIDKAVPK RILDLMNVEG LTRENVASHL QKYRLYLKRV    60

SEQ ID NO: 23            moltype = AA  length = 51
FEATURE                  Location/Qualifiers
REGION                   1..51
                         note = misc_feature - Myb domain of SGI1 polypeptide of SEQ
```

-continued

```
                        ID NO: 9
source                  1..51
                        mol_type = protein
                        organism = unidentified
                        note = Coccomyxa subellipsoidea
SEQUENCE: 23
KKARVVWSVE MHQQFVQAVN QLGIDKAVPK RILDLMNVDG LTRENVASHL Q          51

SEQ ID NO: 24           moltype = AA   length = 61
FEATURE                 Location/Qualifiers
REGION                  1..61
                        note = misc_feature - Myb domain of SGI1 polypeptide of SEQ
                         ID NO: 10
source                  1..61
                        mol_type = protein
                        organism = unidentified
                        note = Ostreococcus lucimarinus
SEQUENCE: 24
KKPRVVWSAE LHAQFVTAVN QLGIDKAVPK RILDLMGVQG LTRENVASHL QKYRLYLKRL  60
Q                                                                 61

SEQ ID NO: 25           moltype = AA   length = 65
FEATURE                 Location/Qualifiers
REGION                  1..65
                        note = misc_feature - Myb domain of SGI1 polypeptide of SEQ
                         ID NO: 11
source                  1..65
                        mol_type = protein
                        organism = Chlamydomonas reinhardtii
SEQUENCE: 25
KKARVVWSVE MHQQFVNAVN QLGIDKAVPK KILEIMGVDG SAGRLADTSG RDVCGTVYRL  60
YLKRV                                                             65

SEQ ID NO: 26           moltype = AA   length = 61
FEATURE                 Location/Qualifiers
REGION                  1..61
                        note = misc_feature - Myb domain of SGI1 polypeptide of SEQ
                         ID NO: 9
source                  1..61
                        mol_type = protein
                        organism = unidentified
                        note = Chromochloris zofingiensis
SEQUENCE: 26
KKPRVVWSVE MHQQFVQAVN QLGIDKAVPK KILELMNVDG LTRENVASHL QKYRLYLKRV  60
Q                                                                 61

SEQ ID NO: 27           moltype = AA   length = 60
FEATURE                 Location/Qualifiers
REGION                  1..60
                        note = misc_feature - Myb domain of SGI1 polypeptide of SEQ
                         ID NO: 10
source                  1..60
                        mol_type = protein
                        organism = unidentified
                        note = Volvox carteri
SEQUENCE: 27
KKARVVWSVE MHQQFVNAVN QLGIDKAVPK KILEIMNVDG LTRENVASHL QKYRLYLKRV  60

SEQ ID NO: 28           moltype = AA   length = 60
FEATURE                 Location/Qualifiers
REGION                  1..60
                        note = misc_feature - Myb domain of SGI1 polypeptide of SEQ
                         ID NO: 11
source                  1..60
                        mol_type = protein
                        organism = Tetraselmis sp.
SEQUENCE: 28
KKQRMNWSDE MHQQFVNAVN QLGIDKAVPK RILDLMSVEG LTRENVASHL QKYRIYLKRM  60

SEQ ID NO: 29           moltype = AA   length = 60
FEATURE                 Location/Qualifiers
REGION                  1..60
                        note = misc_feature - Myb domain of SGI1 polypeptide of SEQ
                         ID NO: 12
source                  1..60
                        mol_type = protein
                        organism = Oocystis sp.
SEQUENCE: 29
KKPRVVWSVE MHQQFVNAVN QLGIDKAVPK RILDLMNVDG LTRENVASHL QKYRLYLKRV  60
```

```
SEQ ID NO: 30              moltype = AA  length = 61
FEATURE                    Location/Qualifiers
REGION                     1..61
                           note = misc_feature - Myb domain of SGI1 polypeptide of SEQ
                            ID NO: 18
source                     1..61
                           mol_type = protein
                           organism = Micromonas sp.
SEQUENCE: 30
KKPRVVWSAE LHQQFVTAVN QLGIDKAVPK RILDLMGVQG LTRENVASHL QKYRLYLKRL    60
Q                                                                   61

SEQ ID NO: 31              moltype = AA  length = 126
FEATURE                    Location/Qualifiers
REGION                     1..126
                           note = misc_feature - Response Regulator receiver domain of
                            SGI1 polypeptide of SEQ ID NO: 6 or 7
source                     1..126
                           mol_type = protein
                           organism = unidentified
                           note = Parachlorella sp.
SEQUENCE: 31
PAGLKVLVVD DDLMCLKVVS AMLKRCSYQV ATCSSGSEAL TLLRERNEDG SSDQFDLVLS    60
DVYMPDMDGF KLLEHIGLEL ELPVIMMSSN GDTNVVLRGV THGAVDFLIK PVRIEELRNV   120
WQHVVR                                                             126

SEQ ID NO: 32              moltype = AA  length = 123
FEATURE                    Location/Qualifiers
REGION                     1..123
                           note = misc_feature - sub-sequence of Response Regulator
                            receiver domain of SGI1 polypeptide of SEQ ID NO: 9
source                     1..123
                           mol_type = protein
                           organism = unidentified
                           note = Coccomyxa subellipsoidea
SEQUENCE: 32
PAGLKVLVVD DDPLCLKVVE HMLRRCNYQV TTCPNGKAAL EKLRDRSVHF DLVLSDVYMP    60
DMDGFKLLEH IGLELDLPVI MMSSNGETNV VLRGVTHGAV DFLIKPVRVE ELRNVWQHVV   120
RRK                                                                123

SEQ ID NO: 33              moltype = AA  length = 122
FEATURE                    Location/Qualifiers
REGION                     1..122
                           note = misc_feature - sub-sequence of Response Regulator
                            receiver domain of SGI1 polypeptide of SEQ ID NO: 10
source                     1..122
                           mol_type = protein
                           organism = unidentified
                           note = Ostreococcus lucimarinus
SEQUENCE: 33
PAGLGVLVVD DDLLCLKVVE KMLKACKYKV TACSTAKTAL EILRTRKEEF DIVLSDVHMP    60
DMDGFKLLEI IQFELALPVL MMSANSDSSV VLRGIIHGAV DYLLKPVRIE ELRNIWQHVV   120
RR                                                                 122

SEQ ID NO: 34              moltype = AA  length = 123
FEATURE                    Location/Qualifiers
REGION                     1..123
                           note = misc_feature - sub-sequence of Response Regulator
                            receiver domain of SGI1 polypeptide of SEQ ID NO: 11
source                     1..123
                           mol_type = protein
                           organism = Chlamydomonas reinhardtii
SEQUENCE: 34
PAGLRLLVVD DDPLCKVVE QMLRKCSYEV TVCSNATTAL NILRDKNTEY DLVLSDVYMP    60
DMDGFRLLEL VGLEMDLPVI MMSSNGDTSN VLRGVTHGAC DYLIKPVRLE ELRNLWQHVV   120
RRR                                                                123

SEQ ID NO: 35              moltype = AA  length = 61
FEATURE                    Location/Qualifiers
REGION                     1..61
                           note = misc_feature - Response Regulator receiver domain of
                            SGI1 polypeptide of SEQ ID NO: 12
source                     1..61
                           mol_type = protein
                           organism = unidentified
                           note = Chromochloris zofingiensis
SEQUENCE: 35
MDGFKLLETV GLELDLPVIM MSSNGEHTTV MRGVTHGACD FLIKPVRIEE LRNIWQHVIR    60
```

```
                                      -continued

R                                                                             61

SEQ ID NO: 36            moltype = AA  length = 123
FEATURE                  Location/Qualifiers
REGION                   1..123
                         note = misc_feature - Response Regulator receiver domain of
                           SGI1 polypeptide of SEQ ID NO: 13
source                   1..123
                         mol_type = protein
                         organism = unidentified
                         note = Volvox carteri
SEQUENCE: 36
PAGLRLLVVD DDPLCLKVVE QMLRKCSYDV TTCTNATMAL NLLRDKSTEY DLVLSDVYMP     60
DMDGFKLLEV VGLEMDLPVI MMSSNGDTSN VLRGVTHGAC DYLIKPVRLE ELRNLWQHVV    120
RRR                                                                  123

SEQ ID NO: 37            moltype = AA  length = 121
FEATURE                  Location/Qualifiers
REGION                   1..121
                         note = misc_feature - Response Regulator receiver domain of
                           SGI1 polypeptide of SEQ ID NO: 14, 15, and 16
source                   1..121
                         mol_type = protein
                         organism = Tetraselmis sp.
SEQUENCE: 37
PAGLRVLVAD NDPASLQQVE KMLKKCSYQV TLCSSGKNSL EILRKRREEF DLVLADANLP     60
DIDGFKLLHV CHTELSLPVV LMSGTSDTQL VMRGVMDGAR DFLIKPLRVE ELKVLWQHLV    120
R                                                                    121

SEQ ID NO: 38            moltype = AA  length = 123
FEATURE                  Location/Qualifiers
REGION                   1..123
                         note = misc_feature - Response Regulator receiver domain of
                           SGI1 polypeptide of SEQ ID NO: 17
source                   1..123
                         mol_type = protein
                         organism = Oocystis sp.
SEQUENCE: 38
PAGLKVLVVD DDPLCLKVID QMLRRCNYAA TTCQSSLEAL ELLRSSKENH FDLVLSDVYM     60
PDMDGFKLLE IIGLEMGLPV IMMSSNGETG VVFRGVTHGA VDFLIKPVRI EELRNLWQHV    120
VRK                                                                  123

SEQ ID NO: 39            moltype = AA  length = 123
FEATURE                  Location/Qualifiers
REGION                   1..123
                         note = misc_feature - Response Regulator receiver domain of
                           SGI1 polypeptide of SEQ ID NO: 18
source                   1..123
                         mol_type = protein
                         organism = Micromonas sp.
SEQUENCE: 39
PIGLRVLVVD DDPLCLKIVE KMLKRCQYEV TTFSRGAEAL KTLRERKDDF DIVLSDVHMP     60
DMDGFKLLEH IALELDIPVM MMSANCATDV VLRGIIHGAV DYLLKPVRIE ELRNIWQHVV    120
RRK                                                                  123

SEQ ID NO: 40            moltype = AA  length = 45
FEATURE                  Location/Qualifiers
REGION                   1..45
                         note = misc_feature - Response Regulator receiver domain of
                           SGI1 polypeptide of SEQ ID NO: 8
source                   1..45
                         mol_type = protein
                         organism = unidentified
                         note = Parachlorella sp.
SEQUENCE: 40
LPVIMMSSNG DTNVVLRGVT HGAVDFLIKP VRIEELRNVW QHVVR                     45

SEQ ID NO: 41            moltype = AA  length = 47
FEATURE                  Location/Qualifiers
REGION                   1..47
                         note = misc_feature - Response Regulator receiver domain of
                           SGI1 polypeptide of SEQ ID NO: 9
source                   1..47
                         mol_type = protein
                         organism = unidentified
                         note = Coccomyxa subellipsoidea
SEQUENCE: 41
LPVIMMSSNG ETNVVLRGVT HGAVDFLIKP VRVEELRNVW QHVVRRK                   47
```

```
SEQ ID NO: 42           moltype = AA   length = 46
FEATURE                 Location/Qualifiers
REGION                  1..46
                        note = misc_feature - Response Regulator receiver domain of
                        SGI1 polypeptide of SEQ ID NO: 10
source                  1..46
                        mol_type = protein
                        organism = unidentified
                        note = Ostreococcus lucimarinus
SEQUENCE: 42
LPVLMMSANS DSSVVLRGII HGAVDYLLKP VRIEELRNIW QHVVRR                    46

SEQ ID NO: 43           moltype = AA   length = 47
FEATURE                 Location/Qualifiers
REGION                  1..47
                        note = misc_feature - Response Regulator receiver domain of
                        SGI1 polypeptide of SEQ ID NO: 11
source                  1..47
                        mol_type = protein
                        organism = Chlamydomonas reinhardtii
SEQUENCE: 43
LPVIMMSSNG DTSNVLRGVT HGACDYLIKP VRLEELRNLW QHVVRRR                   47

SEQ ID NO: 44           moltype = AA   length = 46
FEATURE                 Location/Qualifiers
REGION                  1..46
                        note = misc_feature - Response Regulator receiver domain of
                        SGI1 polypeptide of SEQ ID NO: 12
source                  1..46
                        mol_type = protein
                        organism = unidentified
                        note = Chromochloris zofingiensis
SEQUENCE: 44
LPVIMMSSNG EHTTVMRGVT HGACDFLIKP VRIEELRNIW QHVIRR                    46

SEQ ID NO: 45           moltype = AA   length = 47
FEATURE                 Location/Qualifiers
REGION                  1..47
                        note = misc_feature - Response Regulator receiver domain of
                        SGI1 polypeptide of SEQ ID NO: 13
source                  1..47
                        mol_type = protein
                        organism = unidentified
                        note = Volvox carteri
SEQUENCE: 45
LPVIMMSSNG DTSNVLRGVT HGACDYLIKP VRLEELRNLW QHVVRRR                   47

SEQ ID NO: 46           moltype = AA   length = 45
FEATURE                 Location/Qualifiers
REGION                  1..45
                        note = misc_feature - Response Regulator receiver domain of
                        SGI1 polypeptide of SEQ ID NO: 14
source                  1..45
                        mol_type = protein
                        organism = Tetraselmis sp.
SEQUENCE: 46
LPVVLMSGTS DTQLVMRGVM DGARDFLIKP LRVEELKVLW QHLVR                     45

SEQ ID NO: 47           moltype = AA   length = 46
FEATURE                 Location/Qualifiers
REGION                  1..46
                        note = misc_feature - Response Regulator receiver domain of
                        SGI1 polypeptide of SEQ ID NO: 17
source                  1..46
                        mol_type = protein
                        organism = Oocystis sp.
SEQUENCE: 47
LPVIMMSSNG ETGVVFRGVT HGAVDFLIKP VRIEELRNLW QHVVRK                    46

SEQ ID NO: 48           moltype = AA   length = 47
FEATURE                 Location/Qualifiers
REGION                  1..47
                        note = misc_feature - Response Regulator receiver domain of
                        SGI1 polypeptide of SEQ ID NO: 18
source                  1..47
                        mol_type = protein
                        organism = Micromonas sp.
SEQUENCE: 48
IPVMMMSANC ATDVVLRGII HGAVDYLLKP VRIEELRNIW QHVVRRK                   47
```

```
SEQ ID NO: 49        moltype = DNA  length = 9898
FEATURE              Location/Qualifiers
source               1..9898
                     mol_type = unassigned DNA
                     organism = unidentified
                     note = Parachlorella sp.
SEQUENCE: 49
atggggactt tttcccgcaa atccttctca aacttagcag cactcgctga cggtgacttt    60
gggcagggat ctcaaaacga tttgcgcggt ggtggcccc  tgtctttgag ctcagctgcc   120
aaccgcacct ctcggaactc aatcgatagt gatggcaggc ggctccagcg gtgggtggac   180
caatttttaat cgtctgaaga gtgtataata tgcatcgctt aatctatatg gcgtcttctt  240
gcgaaccagg gctacctgta agcactgcct agtatcgtcc ttaccaattt gttcgcaggc   300
ttatctttgt gagcaaccac ctgccgctcc gcgtttcgaa gggagccacc gactggaatt   360
tcgagtggga cgacgatgcg ttgatcgcgc aggccaagga gggcctgccg gaggacatgg   420
aggcactata tgttggttgc ctccctgtgg aggtggaccc tcaggaccaa gacgtgagca   480
actggggtgc accacagctt tgcaactata tatcccttttg ccactcgctg cttgctgggt  540
gcctgagcaa cggcggaaag ctgacagtgc ttgggtttag agctgcacca gaggcgctgc   600
ctgaagtgac ggttctgttc actgcctccc aagctacgtg tgtgcaactt caatctgtac   660
catgccactg caggaggtca gcctgcagct acagaagcag cacaactgct tccctgtttt   720
tcttgggacg gagctcaaga ccaactatta cagaagtgag gcccatcact gccctgcag   780
cactcttgcc gtctgccccc ccacttcatt ttgcaccata ctcccttttgg gactcaccaa   840
ctgggtgggga cactgttgca ttgcttcctg gcgcatcgtt aggttgggat tgagctgacg   900
caaaccaagg ttgcaccgc  ccctgtgcca aataatcacc gctgggcagc catccttttg    960
ctggccccgg caccagcacc ggcccctgct ccgcctgtgc tctgggcacg gggcacgaaa   1020
aaaaactgct gaatgatgg  agtgatgtgc agggcttgct cgaatgctgg ccaccgcctc   1080
catttgcacc cacagtgtca ccagtcacac atgctgcacc caagcataag ggaagggact   1140
gtgagtggaa gaaagggagg caatgcaatg gaacagaaag gctggagtgc ggggcatact   1200
gtccgcaatc gcaccgcagc caggccttgc gtctgcaaac agagatgcgg tgcacagatg   1260
cagcacacgc ctgccacctg tgtgcgtgag catgcatgtg ctgtgtgtgt gccattgggc   1320
tggtgcagag ttctgcaagc agcagctgtg gccccatcctg cactacctca tcccctcaa   1380
ccccactagc ctaggcaggt ttgacccccgg actctgggcg tcatacgtga gggcgaacaa   1440
ggtaggcgag gtagagctga ggggtggagg agaggggtg gagagggtgg atcatggtga    1500
cgtgtgaagg gaggggagg gtgggtaggt gttgggtggg gtcaggaggg gatgaccatg    1560
tgattgagag cttggtgcac atcctctccc cccttgcaat ggcaggtgaa gtggagaaga   1620
gaaggcaggg gtgtaagatt gggcatagtg tggagtgcag gaaggccttg cgaaaaggaa   1680
gggggggatgc atgcttgctg tgccgtgaca ggcgtgctcc ggctggtgga tctgaaaaca   1740
ttgtgggttg gaggggaatg ccaggaacat tcctgttccc tcttccccgc acccggcctt   1800
atggcaccta agcaccggtc cccgcccact accctaccca ctcacctcca gcttcccct    1860
ggcatatgct ctcaaggtgg ccatagtggc ctcctcgctg ccagccatca cgtatgggtt   1920
gggaggggagg aaaaagggg ggggagggtg gcggtgccac atctaccagg tgcgcgaccc   1980
tagaaaagtc caccgccccc tcttccttca ggtgtttgcg gacaagatgg tggaggtgct   2040
ggggtcgctg gaggacgact ttgtgtgggt gcacgactac cacctgctgg tgctgccctc   2100
gctgctgcgg aaaagattcc acagaatcaa gtgagatccc ggggagcaag caagaccag    2160
cccatgcgtg gttgcatggg ggagtacggg tgcccatgca ggctagtagg ggtgggggtgt  2220
gggaagggggt catttccggg gggagagcgg gggtgtgggt gaggggtctc ttcttcaacc   2280
caccacgttg acgtggcttg cttttggagtc ctgttttatc ctgcattcag ggtttcgtgc   2340
tacgtttgct cgcctcgcac cttttccgtgg aacggttgca tgcccttctc cttcagcggg   2400
gtgctggcac atgcagcccg ttagtgcaat gccattagga ggggggcagg gaggggggga   2460
gtggcatgga aggacgggaa aatgaggcaa aagaggtggg caggtgcaag ggtgtgtagc   2520
tgccaggata ggagggctgg acaccaggta ctaaccccgt gcctggtccg cgctgcaggt   2580
gcggaatctt cctccactcc cccttccct  cctccgaggt gttccgaacc ttcccccggc   2640
gggaagagat catacggtcc atgctgaatg cggatcttat aggtggggca tcacccacca   2700
ccaccaacct tccacttacc ccttcacacc ccatccaccc cttcaccctc gcacagcaat   2760
gttcctcacc taacttgtcc ctatctcata caccagacgt ggacaccccgc accccctcc   2820
ccccatatc  ccctcccccc ccccatact  ccctccccc  cttcgtcctc gcttttaact   2880
cacagctgtg tgcatctatt catatctgaa ccttcctttc ggcaaggtgt tgtcatgggg   2940
ttaagccatg gcacccatc  gctgcagctg cccaccagct tctcgctgtc ccctgtcac    3000
cccgtcaaac acgcccctcc ccaccccccc cccgcaggct ccacaccttt tgactacgcg   3060
cggcacttcc tgtcatgctg cgccccgcatg ctgggactgg agcacaagac cagccggggg   3120
gccatcatca tcgagtacta cggcagggac gtgggcatca aaatcatgcc cacaggtgag   3180
gggaaggggga ggggctgtat tgtgtgctgc gttgtgcgtg cttgggtgtg tccgtgcatg   3240
cgtgtgcgtg ggtgtcattc aatgagtgtg ggggcaggg  ggctcctctg tgtcacgtga   3300
ggggtcacag gccaaggtga gtcaagccaa ccagggttag tcatcgtgc  cagctggctg   3360
cagctgtgtg cgggtgcgga agggccaatc tggccatctg ctgcctgctg gggaggggg   3420
gttgcattgt cccccttcatg ctgcgcatgc tgtgctactt tctggaagcc ctgagagctg   3480
ctgttgactt accagctccc cccccctcct cccccctacc ccaggcgtga agccctcccg   3540
cttcctcagt gccttcagct ggaaggacac agagtggagg aggggggagc tggcggcgca   3600
ggtgagcggc gctggtttgc cgctgataag gggggggttg gggggggca  caataaaata   3660
tgatgttttg ctacaaaatc accctcgacc tcagctcgta gggtgggcaa catgtgggc   3720
gaacggggag ggggggggg ggggggcgag atcccacaga atccgtagga ttcacgaata   3780
tgtacttttg acctttttcaa ccataccctt ttgccgccac ctcccatttc gaagagggcg   3840
ggggggtccc aatcattcag cgtccgggtg gctgccttga ggatatttga tggggcgcca   3900
cccctcccca gcttcctacca gtttcttgct gtctgggcca ttccagtcg  catctttct    3960
ccatcattca cccatgcccc acgttccgtt cccatcaccc cccatgctc  tcctataacc   4020
taaaaatcgg ccaaagacta ggggagcgtc taggtgaaaa ttttttgatta agtacatgaa   4080
aatttcttac gtgcacccca cccacccacc caccccttccc cctgtgcagt tcaagggcaa   4140
gacggtgctg ctgggcatgg acgacttgga cgtgttcaag gggatcgagc tgcggctggc   4200
cgccttcaag gacgtgctgg agtaccaccc ggagtggaag gggaggctgg tgctgctgca   4260
```

```
ggtcaccacc acaaggtgcg cggcaacggg ctgcgttgtg ggttttttcc ccttgttttc   4320
cgttcgcttt tccagttcat aggaaggaaa cagcagatag tacaagttat gccgtgtctg   4380
ttgtctctgt tttttttttt agaaggaaag agagctgatt cattttgagt tcaagttgaa   4440
aaacaacgaa aacatgaaag tgaagagtga ggttcagtca ttggtaggct tcaggcgtgt   4500
gtgggggcgg ggggctgcgg gtcggcacca ccggggttggc ggcagtgaag tgcgttttta   4560
actgtcgggg tgagggcggg catggaaggt cgtgcattgg aagggggcat ggggcggggt   4620
gggatgggta ctgctgctgc aggtgcctcc tgaacgggtg ggtggctgtc tgctgaggct   4680
gtggagggtg cagggcgtag ggcttattct agggtgctga agcggggtga tttcgatgcg   4740
gggctggggt tgcttggtg gagtgcgggt ttggtcctcc attcgccccc ccacccaccc   4800
accctggtgc cgcagggccc ccggccgcga cgtggacgac ctatttgact tcatcacgaa   4860
gcaggtggag gagatcaacg agcggtttgg ggcgccgggg taccagccgg tggtgtggtt   4920
taaccgcccc gtaccatgt acgagcgcat cgccatgctg tccatcgcag gtgaggcgct   4980
tctgcgcttc tgcagtgcaa tgctgctgcg ctgctccact gctgcacttg tgcgctgctg   5040
tgatgcgggt cgtctgtagt cgctgtactg caccccggac ggacaacccc cgcacgcgg   5100
tccccgaggc ggtccgcca ctgcctggcc cttgctgaca tggcggctaa ccctgccctg   5160
ccctgcagac gtggcggtgg tgacggcac gcgtgacggg atgaacctga tgccgtacga   5220
gtacgtggtg tgccgacagg tgcgtcccct ccccccccc cccttgtcc ctgaacctcc   5280
tatgccccac gacccagacc ctgctctatg tccgtgtgcc ctgggaccgc gcttctcaat   5340
tcccacacct gcgctctgct acaccaacag gctcccctg ctccgctgcc tgcgccaccc   5400
cccccctaca gcccccacc actctctcct cccaccctct cctcggcagt tccggatgca   5460
gcaccccag gtgcagggcc cgctctctcc ccactcactg gcagggccag ggcggcggag   5520
aaggaaggct cgtgcccaac tacacggaaa cctgcacctt gacctcgcgt gctggcaggt   5580
tcaggcctat ggggtccagg gtgtgttcgc ctcctcccc tccttacctc agcctgcagg   5640
ttgggtaccc tttcgggct tccctcagaa caccccacc cccccctct ctcctgcagg   5700
gtcccccagg tctggcagag acggagggcc cccgccacag ccagctggtg gtgtcggagt   5760
tgtgggggtg ctcgcctcg ctgtcggggg ccatgcgggt caacccctgg gctggcgaag   5820
cggtacgtac cgcggtgcag agcgcgcagc gccctgcatg gattgctccc ccccccaac   5880
cccctccctt ttaccctgc cgtcaccccc cccccctccc tcctcccatc ccatccaacc   5940
ctgccgccac cctgggggcg ggacgccgtg gcacctctgc ccatcacccc tctttgacac   6000
gtgtccgaac ctttgcggta tgcccagctg cccgagcccc tcgcggca ggagggcccc   6060
gttccaatcg gagcccccat actgctcgtt acactgtatc attcaagttg atgtattttt   6120
gcatacctag agaatgcatt gatgcttgca atttgtcgac tcgtacattt cacatcgtag   6180
ttgttcatgc gatgctaagt ttggtgcaag gtttgtgaag ctagttgaac tcccttccca   6240
caagatttca actgaagttt ttatactttg aagtcgccac acctccatct cacaagggtg   6300
taggagggcg aggttccgtt ctttcacaac aaccgcaacg atttctcgtc gtccagcaac   6360
agcagaagct gttgtgcgca cctgtgcttc aggcgtgggg agtgcatgtg tgcgcaggtc   6420
acacagtcct cccaccctcc ccgccagccc gcccaccaac acactcacgt cgtggtgatg   6480
catccctccc cctttcccct cgcctcctc cccttgcccc ccttcctgcg ctcaccccct   6540
cacctgcttt ccccctccct cctgcaggtc cgggacgcat tgtacggcgc catccgcatg   6600
cccatagagg aacgtcacat ccggcacgag aagcactgga agtacgtctc ctcccacacc   6660
gttcagttct gggccaaggt gagcttgatg cagccgcgc ggtgcgggac caatgtcgca   6720
caccacccag cagcgcacgc agcagggcgg agcagtgctc ttaattgagg tgttaggatt   6780
aggggtttagg gacccaagac cccaagaccc ctcccttcca cacacacaca tgcacacgca   6840
cgcttacccc ttacccacac gctctctctc acacacactg ctgcctcct acaagaagcc   6900
cggcaccgcc cacctgtcac ataccggctt gaaatgccaa ttgcaatgcc ccccccccc   6960
cccccccgc caccccttc ttctccccg cgcagtccta cgtcaccgac ctgcagcgct   7020
tcacggccaa ccacagcaag ctgcagtgct tcgaccttgg gtttgcgctg gacaccttcc   7080
gcatggtggc ccttacctcc aacttcagga agctgcagac cgacactgtg gtcaaggcgt   7140
accagagagtg tgttctttgg ggggggggg ggagagggag taggtagatg cgaaattcgg   7200
tcgttcatgc aggtgtacac aagcttgatt gtcattcatt tcaaaattag acagcaagag   7260
ctcctgtgcc tgatttggtc ccagtggaaa aggactcacg gttgttgtta gatcgatgat   7320
cggagcgagg gaggggaagc ctgctggggg agggggggg atttggcatg ggtggtggtc   7380
tgctgtgtgt gcaggcggtg tggtgtgagg ggttggggca tgcagtcggg tgcagaggtg   7440
cgggtgtgat gagaaaacgg ggggtgctga ccccccccct cccccacct tcccaccgc   7500
tccccccccc ccccccgtt ctacctaggg ccaagaagcg tgtgctgctg ctggaccacg   7560
acggtaccct gatggccccc tcctccatct cctcccgccc caccgaccac gtgctggcca   7620
cgctgcgcca gctcacctcc gacccgcgca acaccgtgta catcatctcc ggccgcgccc   7680
gcaccgagct gcaggagtgg ttcaagtcgg tggtgagtgg cgccccccaa cccctccctt   7740
catcgtcctt actcaccct tgctcatcac ccccgagctg caggagtggt tcaagtcggt   7800
tattagtagc ctacccccc cccccccccc cccaaatctt cttcatcgcc cttcctcacc   7860
ccttacacat caccccacgg ttgcacacgt gcctggcctg gcaccagggc tgcgcccct   7920
actccccccc aagtgtgaaa ccctttggcc aagccggcta aagctgaggt agtgtgcccc   7980
ccgccctccc ccccccact ctcaagcgcc ctgctgtctg ccgctgtgcc ccccctcagc   8040
ggcggtgccc ccctctgt ctcactttg cacacgcagc gcacgcgctc tctctccgcc   8100
ccccccccctc cccccccccc cccgccccc ttgtcaatcc actagttccc ccctgtgtg   8160
tgtcaccccc catgcagccc aacctggggc tggctgcgga gcacggcttc tacctgtgga   8220
ccccccggctc cgccgactgg gcggtgcagg acccggacat ggggtttggg tggaaagaga   8280
ttgtggagcc catcctccag gtgggggtg cggggcagcg ggtcttgcat actcatgcac   8340
tactgactga tgatgaccac gcaaccatgg taggttttgg atgggaggac accgtggagc   8400
ccatcctcca ggtgggggc tcaggcctct cctacctggg catcgcagca aaccgccgtc   8460
cggttctgca tgggcgctgc ctagtgcaca gaaacccagg gggagtcggg gttgctccaa   8520
cccaaccct acgcacagcc caccctggc ttcaccctgg cttcacccct cctacccgcc   8580
acacgcctcg cccctcctt ttccggcccc cctccccc cgcagcaacg cgtgcgcccc   8640
ctccccacct ccgtttctc tctcggaagg caccccct cagaggttga tgtgcgaatg   8700
acgaacttgc cgtcacccc ttttcagcct tgttttccac cgcttcctgg ccctttccac   8760
gccccttttca ccaccctgac gatcctcttc acccccccc cccccttct cgagcaggtg   8820
tacaccgagt ccacgacgg gtcccacatc gaagccaagg aaagcgcgct ggtgtggcac   8880
taccgcgacg ccgaccccga ctttgggtcg tggcaggcca aggagctgct ggaccacctg   8940
gaaggcatca tctccaacga gccagtggag gtcaggcgca cacacccct gccaccccc   9000
```

```
accattcccc tcttccctc ccctcccc tccctccc ctccttctc ccccccccc 9060
gccttcctt cagtcccttc caggagcacc ctgcccgcca ccccccgc cacaccgctc 9120
ctttgtgacc ccggcgttgc gtgctgccgc gccttgcgcc cccaggcag acgccgctgc 9180
gacaaccccc ctccccccc aaaccttct atcccccc cccccccgc ccgcccgtcc 9240
gccccgttc caagcaagca tctacttgca caggcatgca tggcgccatg cgtccacccc 9300
ctgcagggtt gacagtgtgt ccctctccc cttccccct cccccgcc tgctgcagat 9360
tgtggcgggc cagaacatcg tggaggtgaa gccgcaggga gtgagcaagg gcaaggtggt 9420
ggagcgcatc ctgcacgact gcctcaccgc cagccaggcg ccggagttg tgctgtgcgt 9480
ggggacgac agatcaggtg cgggtgggaa gcggggtgtt gggaggggg aagggctggg 9540
ggcacgggcg ggcgggtggc tggattgcag ggcgagcaac aacctccatt ggtgcaaggt 9600
ctgtggtgtg acgtgctgtg ctgtgctgtg ccgtccctgg gtgagccgtg ctgtgctgtg 9660
ctgtgcagac gaggacatgt tcactgccat ggagaacatg cagttctccc cccacatgcc 9720
ggtggaggtg tttgcatgca cggtggggca gaagccgagc aaggcgccct tctacgtcaa 9780
cgacccggca gaggtgggtg gatgtggtag caggatgtgc gggggaagg gggggaagg 9840
ggcgtccgcc cctgaaaccc atgggattgg ggagggggga gggggatgc acctctga 9898

SEQ ID NO: 50        moltype = DNA  length = 900
FEATURE              Location/Qualifiers
misc_feature         1..900
                     note = RNA binding domain, cds, encodes SEQ ID 1
source               1..900
                     mol_type = unassigned DNA
                     organism = unidentified
                     note = Parachlorella sp.
SEQUENCE: 50
atgtcctcgg aggaaataag caaagatatg gaggaagcaa gcagcagcgg ggatggaggg 60
ggaaaattat ttctcggagg tttaagttgg gacacaacgg aagagaaatt aagggaacat 120
tttggcgtat atgcgatat tcacgaagct gtggtcatga aggataggac gactgggcga 180
ccgcgaggat tcggatttgt tactttcaaa gatgcggagg ttgcagacag ggttgttcaa 240
gatatccacg tgattgatgg cagacagata gacgcgaaga aatctgtacc gcaagagcaa 300
aagccgaagg ctcgaaaaat atttgttggc gggctcgcac ctgaaactac agaggcggat 360
ttcaaagagt attttgaacg atatggctcg ataagcgacg ttcaaataat gcaagatcat 420
atgacaggcc ggtcgagggg cttcgggttc attacttttg aggaggacgc agcagtagag 480
aaggtgtttg cccagggcgc catgcaagag cttggtggca agcgcattga aatcaagcat 540
gccactccca aggggtctag ctcaccaacc actcctgggg ggaggagttc tagtggaggc 600
agagggcagg gctatggcag agccatgcca atgcctttcg gtcaacttgc cggatccccc 660
tatgggtatg gcttgtttca cttccctcca ggcgtgatgc cccatgccac ccctacagc 720
atgggctacg ccaacccta cctgatgatg cagcaaatca gcggctaccc cggcgccacg 780
ccgtatccat ttgccggcct gtatggcggg caggggcgtg gagcctcgca gcagctgcag 840
caggctcagc acacgtcaca gcagctgtct tcctcggag cggggcccgt gactcgcctg 900
```

RECOMBINANT ALGAE HAVING HIGH LIPID PRODUCTIVITY

CROSS-REFERENCE TO RELATED APPLICATIONS

This application is a continuation application of U.S. application Ser. No. 17/124,348 filed Dec. 16, 2020, now pending; which claims the benefit under 35 USC § 119(e) to U.S. Application Ser. No. 62/949,378 filed Dec. 17, 2019. The disclosure of each of the prior applications is considered part of and is incorporated by reference in the disclosure of this application.

INCORPORATION OF SEQUENCE LISTING

The material in the accompanying sequence listing is hereby incorporated by reference into this application. The accompanying sequence listing xml file, named SG12240-2_ST26.xml, was created on Dec. 22, 2023 and is 98,965 bytes in size.

BACKGROUND OF THE INVENTION

Field of the Invention

The invention involves the provision of a recombinant algal mutant organisms for the production of lipids.

Background Information

The production of biodiesel fuels presents great opportunities to develop environmentally sound sources of energy that can be obtained at reasonable cost. Efforts have been directed towards using algae or other microorganisms to produce hydrocarbons that can be used as biodiesel due to their high lipid content. Additional specialty chemicals can also be obtained from these organisms and for use in consumer products.

Since algae use energy from sunlight to combine water and carbon dioxide to produce biomass, achieving increased productivity offers the possibility of a carbon neutral fuel source. The development of algal strains with very high lipid productivity for the production of algal-sourced biofuels therefore presents the possibility of a significant reduction in carbon dioxide released into the atmosphere and a consequent reduction in the problem of global warming.

Strategies for increasing algal production of biofuels and other products have included modification of nutrition provided to the organisms, such as cultivating the organisms in nitrogen, phosphorus, or silicon deficient media. Other strategies have included modification of cultivation or environmental protocols, or various efforts directed towards genetic engineering of the organisms. However, wild type algal strains have not been sufficiently productive to permit an economically viable development of this resource. Higher levels of cell productivity are necessary to efficiently utilize this energy source and achieving sufficient productivity remains an important barrier.

SUMMARY OF THE INVENTION

The invention involves methods and recombinant algal mutants that have a genetic modification to a nucleic acid sequence encoding a trehalose biosynthetic enzyme, and/or a genetic modification to a nucleic acid encoding an RNA binding domain Attenuation of either or both of these genes results in a mutant organism with increased lipid productivity. It was also discovered that one, two, three, or more genetic mutations can be accumulated or "stacked" in a particular mutant cell or organism to result in further increases in the production of lipid products. The lipid products of these mutants can be utilized as biofuels or for other specialty chemical products. In some embodiments the recombinant algal mutants that have a genetic modification in a nucleic acid sequence encoding a trehalose biosynthetic enzyme or can have a genetic modification in a nucleic acid sequence encoding an RNA binding domain In other embodiments the algal mutants can have both of these genetic modifications. And in some embodiments, any of these algal mutants can additionally (and optionally) have a genetic mutation to a nucleic acid sequence encoding an SGI1 polypeptide. Each of these algal mutants exhibit increased lipid productivity versus a control algae.

In a first aspect the invention provides a recombinant algal cell having a genetic modification in a nucleic acid sequence encoding a trehalose biosynthesis pathway enzyme; and/or a genetic modification in a nucleic acid sequence encoding an RNA binding domain; wherein the recombinant alga exhibits increased lipid productivity versus a corresponding control algal cell. In one embodiment the genetic modification results in an attenuation of expression of the nucleic acid sequence having the genetic modification. In one embodiment the recombinant alga can has a genetic modification in the nucleic acid sequence encoding the trehalose biosynthesis pathway enzyme and a genetic modification in the nucleic acid sequence encoding the RNA binding domain In any of the embodiments the recombinant alga can be a Chlorophyte alga and, optionally, of the Class Trebouxiophyceae.

In various embodiments the trehalose biosynthesis pathway enzyme can be any one of a trehalose-6-phosphate synthase, or a trehalose-6-phosphate phosphatase, or a trehalose-6-phosphate synthase/phosphatase. In any of the embodiments the recombinant alga can further have an attenuation of a nucleic acid sequence encoding an SGI1 polypeptide. In one embodiment the recombinant alga has a genetic modification in a nucleic acid sequence encoding a trehalose biosynthesis pathway enzyme (e.g., trehalose-6-phosphate synthase/phosphatase), and a genetic modification in a nucleic acid sequence encoding an RNA binding domain, and an attenuation of a nucleic acid sequence encoding an SGI1 polypeptide, and the recombinant alga exhibits increased lipid productivity versus a corresponding control algal cell.

In one embodiment the genetic modification to the nucleic acid sequence encoding the RNA binding domain is a functional deletion. In one embodiment the nucleic acid sequence encoding the trehalose-6-phosphate synthase/phosphatase can have a substitution mutation versus the wild type sequence. In any of the embodiments the nucleic acid sequence encoding the trehalose-6-phosphate synthase phosphatase can have at least 90% sequence identity to SEQ ID NO: 2. In any of the embodiments the nucleic acid sequence encoding the RNA binding domain can have at least 90% sequence identity to SEQ ID NO: 1.

In some embodiments the substitution mutation in the nucleic acid sequence encoding the trehalose-6-phosphate synthase phosphatase is a E723V mutation versus the wild type sequence, and the recombinant algal cell is an alga of the genus *Parachlorella*. The genetic modification of the nucleic acid sequence encoding the trehalose biosynthetic enzyme and the nucleic acid sequence encoding the RNA binding domain can result in an attenuation in the expression of each of the nucleic acid sequences. In various embodiments the recombinant alga has at least 50% or at least 60% or at least 70% or at least 80% or at least 90% or at least 2×greater lipid productivity versus a control algae. And in some embodiments the recombinant alga can have (alone or in addition to greater lipid productivity) at least 50% or at least 60% or at least 70% or at least 80% or at least 90% or at least 2×greater biomass productivity versus a control algae. In some embodiments the recombinant alga has at least 5 grams per square meter per day of lipid production. The recombinant alga can also have a higher biomass productivity per unit time versus a control alga. The recombinant alga can have the stated higher biomass productivity and/or the stated higher total organic carbon production under nitrogen deficient conditions.

In various embodiments the recombinant alga can be a Chlorophyte algae of any of the genera selected from *Chlorella, Parachlorella, Picochlorum, Tetraselmis*, and *Oocystis*.

In another aspect the invention provides a method of producing a composition containing lipids. The methods involve cultivating an algal organism having a genetic modification in a nucleic acid sequence encoding a trehalose biosynthetic enzyme and/or a genetic modification in a nucleic acid sequence encoding an RNA binding domain; and thereby producing a composition containing lipids. In any embodiment the algal organism can also have an attenuation in expression of a nucleic acid sequence encoding an SGI1 polypeptide. Any organism described herein can be cultivated or used in the methods.

In another aspect the invention involves methods of producing a recombinant lipid-producing algal organism. The methods involve introducing a genetic modification into a nucleic acid sequence encoding a trehalose biosynthetic enzyme in an algal organism, and/or introducing a genetic modification into a nucleic acid sequence encoding an RNA binding domain in an algal organism, wherein the genetic modification(s) is/are relative to a corresponding control algal organism; to thereby produce a recombinant lipid-producing algal organism; and wherein the recombinant algal organism exhibits increased lipid productivity versus a corresponding control algal organism not having the attenuation(s). Any organism described herein can be produced in the methods.

In one embodiment the methods involve introducing a genetic modification into the nucleic acid sequence encoding the trehalose biosynthetic pathway enzyme and also introducing a genetic modification into the nucleic acid sequence encoding the RNA binding domain The methods can also involve cultivating the recombinant algal organism to thereby produce a composition containing lipids. In one embodiment the genetic modification(s) is/are introduced by mutagenesis. In any embodiment the algal organism is a Chlorophyte alga. In various embodiments the trehalose biosynthesis pathway enzyme can be trehalose-6-phosphate synthase, a trehalose-6-phosphate phosphatase, or a trehalose-6-phosphate synthase/phosphatase. In any of the embodiments the methods can also involve introducing a genetic modification into a nucleic acid sequence encoding an SGI1 polypeptide.

In some embodiments the genetic modification(s) to any one or more of the nucleic acid sequences is a functional deletion. In one embodiment the trehalose-6-phosphate biosynthetic enzyme is synthase/phosphatase and its genetic modification is a substitution mutation versus the wild type sequence. In one embodiment the nucleic acid sequence encoding the trehalose-6-phosphate synthase phosphatase has at least 90% sequence identity to SEQ ID NO: 2. In any embodiment the nucleic acid sequence of the algal organism encoding the RNA binding domain is a functional deletion. The nucleic acid sequence encoding the RNA binding domain in the algal organism can have at least 90% sequence identity to SEQ ID NO: 1.

In any of the embodiments the alga can be of the Class Trebouxiophyceae. In one embodiment the substitution mutation in the nucleic acid sequence encoding the trehalose-6-phosphate synthase phosphatase is an E723V mutation and the recombinant algal cell is an alga of the genus *Parachlorella*. In any embodiment the genetic modification (s) can be an attenuation in the expression of the nucleic acid sequence(s). In various embodiments the algal organism can have at least 50% greater lipid productivity versus the corresponding control algal, or at least 75% greater lipid productivity versus the corresponding control alga. The algal organism can also have at least 5 grams per square meter per day of lipid production. The algal organism can have higher biomass productivity per unit time and/or higher biomass productivity under nitrogen deficient conditions and/or higher total organic carbon production under nitrogen deficient conditions.

In any of the embodiments the recombinant alga can be a Chlorophyte alga of a genus selected from the group consisting of: *Chlorella, Parachlorella, Picochlorum, Tetraselmis*, and *Oocystis*. In one embodiment the recombinant alga is an alga of the class Chlorellales.

In one embodiment the method further involves a step of treating the algal organism with uv radiation prior to the step of cultivating. The method can also involve harvesting a lipidic composition from the algal organism.

BRIEF DESCRIPTION OF THE DRAWINGS

FIG. 1B shows aerial lipid productivity (as TOC) as the mean of the first two days in nitrogen deplete conditions.

In FIG. 2B, RBD repair in the SGI1+Tre6P+RBD strain resulted in increased FAME productivity for the first few days of nitrogen starvation until falling to the same levels as the SGI1-KO strain by Day 6. FIG. 2C shows the results for semi-continuous urea batch assay under 2 days of nitrogen deplete conditions for the triple mutation strain (STR0600, i.e., SGI1+RBD+Tre6P mutations) compared to the wild-type *Parachlorella* sp. strain. FAME production for STR600 was 53% higher.

In FIG. 3A RBD recapitulation strain (SGI1+RBD) shows areal FAME productivity equivalent to the SGI1 mutant in the early stages of nitrogen starvation but increases to almost to the levels of the triple mutant (STR00600) levels by Day 6. In the SGI1+RBD strain, the RBD SNP was introduced into a SGI1-only strain. In FIG. 3B, Tre6P repair in the STR0600 triple mutant showed decreased FAME productivity relative to triple mutant STR0600 early in nitrogen starvation but approaches the same level as the triple mutant by Day 5.

FIG. 4A shows increased FAME productivity for the SGI1-KO/RBD/Tre6P stacked mutation strains, similar to the triple mutant STR0600. FIG. 4B shows TOC data for the same.

FIG. 5A shows the STR600 triple mutant (SGI1+RBD+Tre6P) versus SGI1 repair strains 680 and 681 (which have SGI1 mutation repaired) and repair strain 682 (which has RBD mutation repaired). FAME accumulation after 2 days is reduced for the repair strains versus the triple mutant (STR0600), but still higher than the SGI1-only mutants. FIG. 5B shows similar data with respect to TOC accumulation after 2 days.

DETAILED DESCRIPTION OF THE INVENTION

Figure 1A:
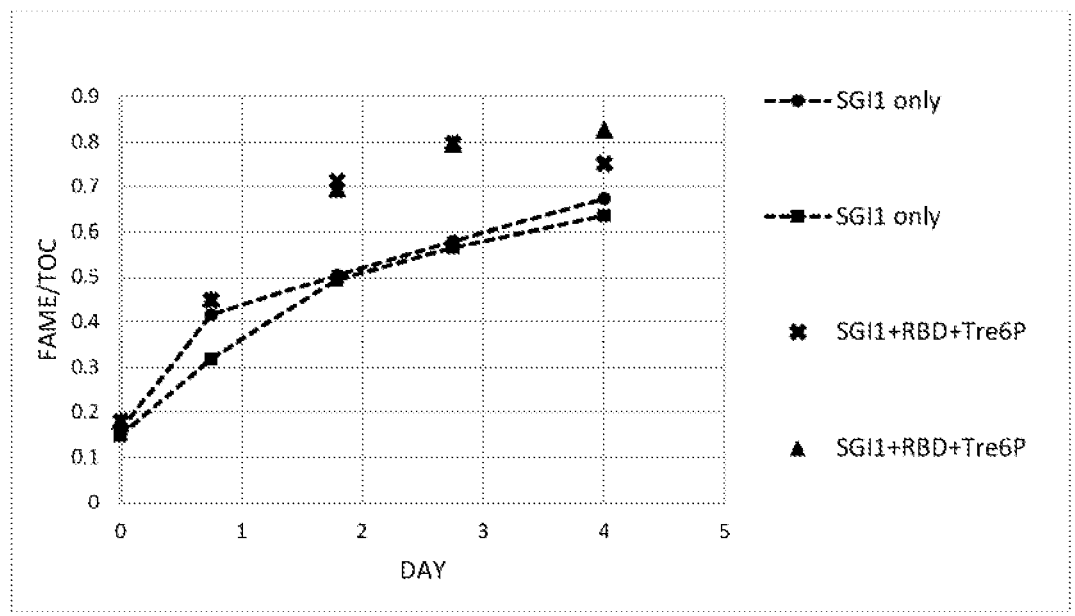
FIGS. 1A-1B, FIG. 1A provides a graphical illustration of a FAME/TOC productivity plot for strains isolated from BODIPY-FACS enrichment after 2-days of nitrogen deplete conditions, showing the amount of fixed carbon that is partitioned to lipids and nitrogen-deplete lipid productivity.

The invention provides recombinant algal mutants that have a genetic modification to a nucleic acid sequence encoding a trehalose biosynthetic pathway enzyme, and/or a genetic modification to a nucleic acid encoding an RNA binding domain A genetic modification to either or both of these genes as described herein results in a recombinant or mutant cell or organism with higher productivity, for example higher lipid productivity. The recombinant cells or organisms can also have a higher biomass productivity. The recombinant algal mutants can also optionally have reduced chlorophyll content and/or a reduced PSII antenna size. Any of the algal mutants described herein can also, optionally, have an attenuation of a gene encoding an SGI1 polypeptide. Thus, in some embodiments the algal mutants have 1) a genetic modification to a nucleic acid sequence encoding a trehalose biosynthetic pathway enzyme, and/or 2) a genetic modification to a nucleic acid encoding an RNA binding domain; and, additionally and optionally 3) a genetic modification in a gene encoding an SGI1 polypeptide. Any of the recombinant cells or organisms disclosed herein can be mutant photosynthetic organisms. It was discovered unexpectedly that the genetic mutations disclosed herein can be accumulated or "stacked" in a cell or organism to result in further significant increases in the production of lipid products made by the cells or organisms, which further increases can be additive, more than additive, synergistic, or exponential. The stacking can be performed by recapitulating more than one of the mutations in a wild-type or other background cell or organism. The recombinant algal cells or organisms disclosed can have one, two, three, or more than two, or more than three genetic mutations described herein, and thus can have the desirable characteristics disclosed herein.

The recombinant cells or organisms of the invention can have higher FAME and/or biomass productivity than corresponding control cells or organisms that do not have a corresponding attenuation(s) of the nucleic acid sequence encoding an RBD domain and/or a nucleic acid sequence encoding a trehalose biosynthetic pathway enzyme and, optionally with either or both, a nucleic acid sequence encoding an SGI1 polypeptide, or any combination or sub-combination of these attenuations, and that are cultivated in the same or substantially the same conditions. Biomass productivity can be measured as the rate of biomass accumulation, for example, the total organic carbon content of the respective cells or organisms, which in one embodiment can be in batch cultures. Batch culture is a culture where nutrients are not renewed or re-supplied to the medium during the time period the cells or organisms are cultured. Any of the mutant cells or organisms disclosed herein can be photosynthetic cells or organisms. Any of the recombinant cells or organisms described herein can exhibit increased lipid and/or biomass productivity under photoautotrophic conditions. Corresponding (control) cells or organisms are useful for evaluating the effect of any one or more genetic modifications. Corresponding (control) cells or organisms do not have the one or more genetic modifications being evaluated and are subjected to the same or substantially the same culturing conditions as the test cells or organisms such that a difference in the performance of the cells or organisms is based only on the genetic modification(s) being evaluated. Corresponding (control) cells or organisms can be of the same species as the test organism. They can also be the same or similar in every way except for the one or more genetic modification(s) being evaluated. In some embodiments the corresponding (control) cell or organism is a wild-type cell or organism.

In one embodiment the recombinant cells or organisms are algal cells. In one embodiment the recombinant alga has a genetic modification to a nucleic acid sequence encoding a trehalose biosynthetic enzyme. In another embodiment the recombinant alga has a genetic modification to a nucleic acid sequence encoding a RNA binding domain In another embodiment the recombinant alga can have a genetic modification to a nucleic acid encoding a trehalose biosynthetic pathway enzyme and a genetic modification to a nucleic acid sequence encoding an RNA binding domain Additionally, and optionally any of the recombinant alga can further have a genetic modification to a nucleic acid sequence encoding an SGI1 polypeptide with the genetic modification encoding an RNA binding domain and/or a genetic modification to a nucleic acid encoding a trehalose biosynthetic pathway enzyme.

The lipid products of these mutants can be further processed into biofuels or used in the production of other specialty chemical products. The nucleic acid sequences encoding the trehalose biosynthetic pathway enzyme, or the RNA binding domain, or the SGI1 polypeptide can be any of the nucleic acid sequences described herein, hereby disclosed in all possible combinations and sub-combinations.

In some embodiments any of the recombinant cells or organisms of the invention have a reduced amount of chlorophyll b, and can have an increased chlorophyll a:chlorophyll b ratio compared to a corresponding control cell or organism. The recombinant cells or organisms can have decreased photosynthetic antenna size, for example reduced photosystem II (PSII) and/or reduced photosystem I (PSI) antenna size. In various embodiments the cross-sectional unit size of the PSII and/or PSI antenna of the recombinant cells or organisms disclosed herein can be reduced by at least 10%, at least 20%, at least 30%, at least 25%, at least 30%, at least 35%, at least 40%, at least 45%, at least 50%, or at least 60% compared to the PSII and/or PSI antenna size of a corresponding control cell or organism. The recombinant cells or organisms can have higher growth rate and/or higher biomass productivity than a corresponding control cell or organism not having the genetic modification, for example, higher biomass productivity per hour or per day or per period of 2 days or 3 days or 4 days or 5 days or 6 days. "Biomass" refers to cellular mass, whether of living or dead cells. Biomass productivity, or biomass accumulation, or growth rate, can be measured by any means accepted in the art, for example as ash free dry weight (AFDW), dry weight, wet weight, or total organic carbon (TOC) productivity. In any embodiment biomass productivity, or biomass accumulation, or the growth rate, can be measured as total organic carbon (TOC) productivity.

The recombinant cells or organisms of the invention can produce a greater amount of a bioproduct per time period (e.g., per minute or per hour or per day or per period of 2 days or 3 days or 4 days or 5 days or 6 days.), for example a lipid product, FAME profile, a carbohydrate, a protein product, a polyketide, a terpenoid, a pigment, an antioxidant, a vitamin, one or more nucleotides, one or more nucleic acids, one or more amino acids, one or more carbohydrates, an alcohol, a hormone, a cytokine, a peptide, or a polymer than a corresponding (control) organism not having the genetic modification(s) and being tested and cultured under substantially the same conditions over the same period of time. The amount of product can be expressed as g/time period, mg/time period, ug/time period, or any other defined quantity per defined time period described herein. Such bioproducts can be isolated from a lysate of any of the recombinant cells or organisms of the invention. In some embodiments, the recombinant cells or organisms of the invention produce at least 10%, at least 15%, at least 20%, at least 25%, at least 30%, at least 35%, at least 40%, at least 45%, at least 50%, at least 60%, at least 70%, at least 80%, at least 90% or at least 100% more of a bioproduct than a corresponding control alga cultured under the substantially the same conditions, which can be batch, semi-continuous, or continuous culture conditions and may be nutrient replete culture conditions or may be nitrogen deplete conditions, and may be photoautotrophic conditions.

Without wanting to be bound by any particular theory it is believed that the genetic modification(s) described herein result(s) in an attenuation of expression of a nucleic acid sequence encoding the trehalose biosynthetic pathway enzyme and/or a nucleic acid sequence encoding the RNA binding domain and, optionally with either or both, a nucleic acid sequence encoding the SGI1 polypeptide. These one or more attenuations result in a significant increase in the amount of lipids produced by the cell, as demonstrated by the total FAME produced by the cell. They can also result in a significant increase in biomass productivity, as demonstrated by the organic carbon produced by the cell (as measured, for example, by total organic carbon).

As used herein, "exogenous" with respect to a nucleic acid or gene indicates that the nucleic acid or gene has been introduced (e.g., "transformed") into an organism, microorganism, or cell by human intervention. Typically, such an exogenous nucleic acid is introduced into a cell or organism via a recombinant nucleic acid construct. An exogenous nucleic acid can be a sequence from one species introduced into another species, i.e., a heterologous nucleic acid. A "heterologous" nucleic acid can also be an exogenous synthetic sequence not found in the species into which it is introduced. An exogenous nucleic acid can also be a sequence that is homologous to an organism (i.e., the nucleic acid sequence occurs naturally in that species or encodes a polypeptide that occurs naturally in the host species) that has been isolated and subsequently reintroduced into cells of that organism. An exogenous nucleic acid that includes a homologous sequence can often be distinguished from the naturally-occurring sequence by the presence of non-natural sequences linked to the exogenous nucleic acid, e.g., non-native regulatory sequences flanking the homologous gene sequence in a recombinant nucleic acid construct. Alternatively, or in addition, a stably transformed exogenous nucleic acid can be detected and/or distinguished from a native gene by its juxtaposition to sequences in the genome where it has integrated. Further, a nucleic acid is considered exogenous if it has been introduced into a progenitor of the cell, organism, or strain under consideration.

A "recombinant" or "engineered" nucleic acid molecule is a nucleic acid molecule that has been altered through human manipulation. As non-limiting examples, a recombinant nucleic acid molecule includes any nucleic acid molecule that: 1) has been partially or fully synthesized or modified in vitro, for example, using chemical or enzymatic techniques (e.g., by use of chemical nucleic acid synthesis, or by use of enzymes for the replication, polymerization, digestion (exonucleolytic or endonucleolytic), ligation, reverse transcription, transcription, base modification (including, e.g., methylation), integration or recombination (including homologous and site-specific recombination) of nucleic acid molecules); 2) includes conjoined nucleotide sequences that are not conjoined in Nature; 3) has been engineered using molecular biology techniques such that it lacks one or more nucleotides with respect to the naturally occurring nucleic acid molecule sequence; and/or 4) has been manipulated using molecular biology techniques such that it has one or more sequence changes or rearrangements with respect to the naturally occurring nucleic acid sequence. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector.

When applied to organisms, the terms "transgenic" "transformed" or "recombinant" or "engineered" or "genetically engineered" refer to organisms that have been manipulated by introduction of an exogenous or recombinant nucleic acid sequence into the organism, or by genetic manipulation of native sequences (which are therefore then recombinant). In some embodiments the exogenous or recombinant nucleic acid can express a heterologous protein product. Non-limiting examples of such manipulations include gene knockouts, targeted mutations and gene replacement, gene replacement, promoter replacement, deletions or insertions, disruptions in a gene or regulatory sequence, as well as introduction of transgenes into the organism. For example, a transgenic microorganism can include an introduced exogenous regulatory sequence that enables transcription in the organism operably linked to an endogenous gene of the transgenic microorganism. Recombinant or genetically engineered organisms can also be organisms into which constructs for gene "knock down," deletion, attenuation, or disruption have been introduced to perform the indicated manipulation. Such constructs include, but are not limited to, RNAi, microRNA, shRNA, antisense, and ribozyme constructs. Also included are organisms whose genomes have been altered by the activity of meganucleases or zinc finger nucleases. A heterologous or recombinant nucleic acid molecule can be integrated into a genetically engineered/recombinant organism's genome or, in other instances, not integrated into a recombinant/genetically engineered organism's genome, or can be present on a vector or other nucleic acid construct. As used herein, "recombinant microorganism" or "recombinant host cell" includes progeny or derivatives of the recombinant microorganisms of the disclosure. Because certain modifications may occur in succeeding generations from either mutation or environmental influences, such progeny or derivatives may not, in fact, be identical to the parent cell, but are still included within the scope of the term as used herein.

The term "Pfam" refers to a large collection of protein domains and protein families maintained by the Pfam Consortium and available at several sponsored world wide web sites, including: pfam.sanger.ac.uk/ (Welcome Trust, Sanger Institute); pfam.sbc.su.se (Stockholm Bioinformatics Center); pfam.janelia.org/ (Janelia Farm, Howard Hughes Medical Institute); pfam.jouy.inra.fr/(Institut national de la Recherche Agronomique); and pfam.ccbb.re.kr. Pfam domains and families are identified using multiple sequence alignments and hidden Markov models (HMMs). Pfam-A family or domain assignments are high quality assignments generated by a curated seed alignment using representative members of a protein family and profile hidden Markov models based on the seed alignment. (Unless otherwise specified, matches of a queried protein to a Pfam domain or family are Pfam-A matches.) All identified sequences belonging to the family are then used to automatically generate a full alignment for the family (Sonnhammer (1998) Nucleic Acids Research 26, 320-322; Bateman (2000) Nucleic Acids Research 26, 263-266; Bateman (2004) Nucleic Acids Research 32, Database Issue, D138-D141; Finn (2006) Nucleic Acids Research Database Issue 34, D247-251; Finn (2010) Nucleic Acids Research Database Issue 38, D211-222). By accessing the Pfam database, for example, using any of the above-reference websites, protein sequences can be queried against the HMMs using HMMER homology search software (e.g., HMMER2, HMMER3, or a higher version, hmmer.janelia.org/). Significant matches that identify a queried protein as being in a pfam family (or as having a particular Pfam domain) are those in which the bit score is greater than or equal to the gathering threshold for the Pfam domain. Expectation values (e values) can also be used as a criterion for inclusion of a queried protein in a Pfam or for determining whether a queried protein has a particular Pfam domain, where low e values (much less than 1.0, for example less than 0.1, or less than or equal to 0.01) represent low probabilities that a match is due to chance.

The recombinant cells or organisms described herein can be generated by human intervention, for example, by classical mutagenesis or genetic engineering, or by any feasible mutagenesis method, including but not limited to UV irradiation, CRISPR/Cas9, cre/lox, gamma irradiation, or chemical mutagenesis. And screening methods can be used to identify mutants having desirable characteristics (e.g., reduced chlorophyll and increased productivity. Methods for generating mutants of photosynthetic organisms using classical mutagenesis, genetic engineering, and phenotype or genotype screening are well-known in the art.

Algal Cell or Organism

The recombinant algal cell or organism of the invention can be a mutant microalga, or a mutant photosynthetic organism, or a mutant green alga. The recombinant alga can be any eukaryotic microoalga such as, but not limited to, a Chlorophyte, an Ochrophyte, or a Charophyte alga. In some embodiments the mutant microalga can be a Chlorophyte alga of the taxonomic Class Chlorophyceace, or of the Class Chlorodendrophyceae, or the Class Prasinophyceace, or the Class Trebouxiophyceae, or the Class Eustigmatophyceae. In some embodiments, the mutant microalga can be a member of the Class Chlorophyceace, such as a species of any one or more of the genera *Asteromonas, Ankistrodesmus, Carteria, Chlamydomonas, Chlorococcum, Chlorogonium, Chlorodendrales, Chloroellales, Chrysosphaera, Dunaliella, Haematococcus, Monoraphidium, Neochloris, Oedogonium, Pelagomonas, Pleurococcus, Pyrobotrys, Scenedesmus,* or *Volvox*. In other embodiments, the mutant microalga can be a member of the Class Chlorodendrophyceae, such as a species of any one or more of the genera *Prasinocladus, Scherffelia,* or *Tetraselmis*. In further alternative embodiments, the mutant alga can be a member of the Class Prasinophyceace, optionally a species of any one or more of the genera *Ostreococcus* or *Micromonas*. Further alternatively, the mutant microalga can be a member of the Class Trebouxiophyceae, and optionally of the Order Chlorellales, and optionally a genera selected from any one or more of *Botryococcus, Chlorella, Auxenochlorella, Heveochlorella, Marinichlorella, Oocystis, Parachlorella, Pseudochlorella, Tetrachlorella, Eremosphaera, Franceia, Micractinium, Nannochloris, Picochlorum, Prototheca, Stichococcus,* or *Viridiella*, or any of all possible combinations or sub-combination of the genera. In another embodiment the recombinant alga is a Chlorophyte alga of the Class Trebouxiophyceae, the Order Chlorellales, the Family Oocystaceae, Chlorellaceae, or Eustigmatophyceae, and optionally a genera selected from one or more of *Oocystis, Parachlorella, Picochlorum, Nannochloropsis,* and *Tetraselmis*. The recombinant alga can also be from the genus *Oocystis*, or the genus *Parachlorella*, or the genus *Picochlorum*, or the genus *Tetraselmis*, or from any of all possible combinations and sub-combinations of the genera.

In various embodiments the recombinant alga of the invention can have a genetic modification to a nucleic acid encoding a trehalose biosynthetic enzyme, or an RNA binding protein, or both. Any of the recombinant alga of the invention can also, optionally, have a genetic modification to a nucleic acid encoding an SGI1 polypeptide. In one embodiment the recombinant alga of the invention has a genetic modification to a nucleic acid sequence encoding a trehalose biosynthetic enzyme, a genetic modification to a nucleic acid sequence encoding an RNA binding protein, and a genetic modification to a nucleic acid encoding an SGI1 polypeptide. In one embodiment each of these genetic modifications is to a native or endogenous sequence of the cell or organism.

A "genetic modification" can denote any one or more of a deletion, a mutation, a disruption, an insertion, an inactivation, an attenuation, a rearrangement, one or more point mutations, a frameshift mutation, an inversion, a "knock out", a "knock in", that results in a physical change to the modified gene, and that reduces or eliminates expression of the one or more gene products. The genetic modification (e.g., to a gene or nucleic acid sequence encoding a trehalose biosynthetic pathway enzyme or RBD domain, or SGI1 polypeptide) can occur in any sequence that affects expression of the gene or the nature or quantity of its product, for example to the coding or non-coding sequence, regulatory sequence, promoter, terminator, exon, intron, 3' or 5' UTR. The genetic modification can be to the host cell's native genome. In some embodiments, for example, a recombinant cell or organism having attenuated expression of a gene as disclosed herein can have one or more mutations, which can be one or more nucleobase changes and/or one or more nucleobase deletions and/or one or more nucleobase insertions, into the region of a gene 5' of the transcriptional start site, such as, in non-limiting examples, within about 2 kb, within about 1.5 kb, within about 1 kb, or within about 0.5 kb of the known or putative transcriptional start site, or within about 3 kb, within about 2.5 kb, within about 2 kb, within about 1.5 kb, within about 1 kb, or within about 0.5 kb of the translational start site.

In one embodiment the genetic modification(s) can be an attenuation (but the genetic modification(s) can also be a deletion or a disruption). An "attenuation" refers to a nucleic acid sequence or gene whose function, activity, or expression is reduced compared to the amount of function, activity, or expression in a corresponding (control) organism not having the genetic modification being examined, where the cell is cultivated under the same or substantially the same conditions, i.e., the diminished function, activity, or expression is due to the genetic modification. In various embodiments an attenuated nucleic acid sequence or gene produces less than 70% or less than 50% or less than 30% or less than 20% or less than 10% or less than 5% or less than 1% of its function, activity, or expression than in a corresponding cell not having the genetic modification at issue under the same or substantially the same culturing conditions. The terms deletion cassette and disruption cassette are used interchangeably. Substantially the same conditions can be the same conditions or slightly different conditions where the change does not materially affect the function, activity, or expression of the nucleic acid sequence modified.

In various embodiments the genetic modification can be a deletion or a disruption. An unmodified nucleic acid sequence present naturally in the organism denotes a natural, endogenous, or wild type sequence. In a deletion at least part of the nucleic acid sequence is deleted, but a deletion can also be accomplished by disrupting a gene (e.g., a "knock out" mutation), or through, for example, the insertion (insertional mutation) of another sequence (e.g., a selection marker), or a combination of deletion and insertion, but a deletion can also be performed by other genetic modifications known to those of ordinary skill that result in the gene not being functionally expressed. A "disruption" of a gene is a functional deletion by insertion or deletion of a nucleotide sequence into or from the coding, non-coding, or regulatory portion of a gene with resulting partial or complete loss of function, activity, or expression of the gene. Functional expression refers to the expression of a functional product or activity of a nucleic acid sequence; when the expressed product of a nucleic acid is a polypeptide a functional polypeptide has at least some of the normal activity of the encoded polypeptide. For a nucleic acid a functional activity is at least some of the normal activity of the nucleic acid. A functional deletion or disruption removes at least so much of the expression or activity of a nucleic acid sequence that the product or activity of the nucleic acid sequence has no significant effect on the cell or organism compared to the natural or normal level of expression, i.e., the cell performs the same as a "knock out" deletion or disruption (e.g., with regard to lipid productivity or biomass productivity). When the nucleic acid sequence encodes a polypeptide, the encoded polypeptide will not be expressed in an amount that makes a significant difference in the cell or organism compared to expression in the unmodified cell or organism. When the nucleic acid sequence has an activity other than encoding a polypeptide the activity is not sufficient to display a significant effect compared to activity in the unmodified cell or organism. In some embodiments the functional deletion can remove all expression or activity of the nucleic acid sequence. In some embodiments the functional deletion is a knockout deletion. Thus, deletions, functional deletions, and disruptions can also be attenuations.

The recombinant cells or organisms of the invention can have a reduced functional absorption cross section of PSII or reduced PSII antenna size. For example, the cross-sectional unit size of the PSII antenna can be reduced by at least about 10%, at least 20%, at least 30%, at least 25%, at least 30%, at least 35%, at least 40%, at least 45%, at least 50%, at least 60%, at least about 70%, or at least about 80% compared to the PSII antenna size of the corresponding (control) cell or organism. The recombinant cells or organisms of the invention can additionally have a reduced functional absorption cross section of PSI or reduced PSI antenna size. For example, the cross-sectional unit size of the PSI antenna can be reduced by at least 10%, at least 20%, at least 30%, at least 25%, at least 30%, at least 35%, at least 40%, at least 45%, at least 50%, or at least 60% compared to the PSI antenna size of a control photosynthetic organism.

In various embodiments, a mutant photosynthetic organism as provided herein can have increased Fv/Fm with respect to a corresponding control photosynthetic organism. For example, the mutant photosynthetic organism may have Fv/Fm increased by at least 5%, at least 10%, at least 12%, at least 15%, at least 20%, at least 30%, at least 40% or at least 50% compared to a corresponding (control) photosynthetic organism. In various embodiments the Fv/Fm can be increased by between about 5% and about 50%, or between about 5% and 30%, or between 5% and 20% with respect to a control photosynthetic organism.

Further, a mutant photosynthetic organism as provided herein can have an increased rate of electron transport on the acceptor side of photosystem II with respect to a control or wild type cell. The rate can be at least about 20%, 30%, 40%, 50%, 60%, 80%, or 100% higher compared to a corresponding control or wild type organism. In addition, mutant photosynthetic cells or organisms of the invention can have a rate of carbon fixation (Pmax (C)) in a recombinant cell or organism as provided herein can be elevated with respect to a control organism. For example, Pmax (14C) can be increased by at least about 20%, 30%, 40%, 50%, 60%, 80%, or 100% compared to a corresponding control or wild type organism.

In some embodiments, the recombinant cells or organisms of the invention have decreased PSI and/or PSII antenna size and can optionally also have a higher amount of a ribulose bisphosphate carboxylase activase (Rubisco activase or "RA") than a corresponding (control) or wild type organism, for example, at least 1.2, 1.4, 1.6, 1.8, 2, 2.2, or 2.5 fold the amount of RA as a control organism. In some embodiments, the mutants demonstrate reduced expression of 6, 8, 10, 12, or 14 LHCP genes and increased expression of an RA gene, such as an RA-a or RA-P gene. Thus, the recombinant cells or organisms of the invention can be mutant photosynthetic organisms having reduced chlorophyll and reduced PSII antenna size where the mutants have a higher amount of Rubisco activase than control photosynthetic organisms.

The LHC super-gene family encodes the light-harvesting chlorophyll a/b-binding (LHC) proteins that constitute the antenna system of the photosynthetic apparatus. A recombinant algal mutant of the invention can also have a reduced expression of LHC genes. Thus, in some embodiments the recombinant cells or organisms of the invention have at least 6, at least 8, at least 10, or at least 12 LHC genes that are attenuated or downregulated with respect to their expression level in a corresponding (control) cell or organism. In various embodiments the reduction in expression of the LHC genes can be a reduction of at least 20%, or at least 30%, or at least 40%, or at least 50%, or at least 60%, or at least 70% in the level of LHC transcripts.

Trehalose Biosynthetic Pathway Enzymes

The biosynthesis of trehalose is an important process and several biosynthesis pathways for the provision of trehalose have developed. The most common biosynthesis pathways involve trehalose biosynthetic pathway enzymes, which include: 1) trehalose-6-phosphate synthase (T6PS), which converts glucose-6-phosphate and UDP-glucose into trehalose-6-phosphate (T6P); 2) trehalose-6-phosphate phosphatase (T6PP), which dephosphorylates T6P into trehalose; 3) trehalase, which converts trehalose into glucose; 4) trehalose phosphate hydrolase, which converts T6P into glucose and UDPG+glucose-6-phosphate; and 5) trehalose-6-phosphate synthase/phosphatase (T6PS/P), which has both the synthase and phosphatase activity of 1) and 2) above in the same enzyme molecule.

The recombinant alga of the invention can have a genetic modification to a gene or nucleic acid sequence encoding any one or more of the trehalose biosynthetic pathway enzymes or any combination of them, which are hereby disclosed in all possible combinations and sub-combinations as if set forth fully herein. In one embodiment the genetic modification is to one or more gene(s) or nucleic acid sequence(s) encoding a trehalose-6-phosphate synthase (T6PS). In another embodiment the genetic modification is to one or more nucleic acid sequence(s) or gene(s) encoding a trehalose-6-phosphate phosphatase (T6PP). In another embodiment the genetic modification is to one or more nucleic acid sequence(s) or gene(s) encoding a trehalose-6-phosphate synthase/phosphatase (T6PS/P). In another embodiment the genetic modification is to one or more nucleic acid sequence(s) or gene(s) encoding a trehalose phosphate hydrolase. In another embodiment the genetic modification is to one or more nucleic acid sequence(s) or gene(s) encoding a trehalase. In some embodiments the genetic modification can be to a promoter, terminator, binding site, or other regulatory sequence for a gene encoding the named biosynthetic pathway enzyme. The regulatory sequence may control transcription or translation of the encoded enzyme. In another embodiment the genetic modification is to any combination or sub-combination of the above one or more nucleic acid sequence(s) or gene(s), e.g., to T6PP and T6PS. But any combination or sub-combination of the recited nucleic acid sequences (or genes) can be genetically modified to achieve the desired effect. In a specific embodiment the genetic modification is an attenuation (e.g., to T6PS/P, or to T6PS and T6PP). In another embodiment the attenuation is a deletion.

In one embodiment the recombinant cells or organisms of the invention have a genetic modification to a gene or nucleic acid sequence encoding a trehalose-6-phosphate synthase/phosphatase (T6PS/P) in a trehalose biosynthetic pathway. For example, a modified organism of the invention (a Chlorophyte alga *Parachlorella* sp.) was found to have a nucleic acid sequence encoding a T6PS/P of SEQ ID NO: 2. This enzyme shows about 30% sequence identity to T6PP from *Candida albicans*. SEQ ID NO: 2 has a genetic modification (versus the unmodified "wild type" organism) at position 273 where a glutamic acid (E273) in the wild-type was changed to valine in the modified organism, which has increased biomass and/or lipid productivity. The E273 is conserved across species, but in some species the corresponding amino acid residue is an Asp. This residue can also be changed to Val in conserved sequences of other species or changed to another amino acid of similar chemical class in the corresponding position to achieve the high lipid phenotype exhibited by the mutant cells or organisms of the invention. For example, instead of a Val another nonpolar amino acid could be substituted such as, for example, any of Gly, Ala, Leu, Ile, Ser, Asn, Gln, Asp, or Met. Thus, in some embodiments the mutant cells or organisms of the invention have an E273V mutation, or a D273V mutation, or a E273X or D273X mutation, where X is any one of Gly, Ala, Leu, Ile, Ser, Asn, Gln, Asp, or Met.

In various embodiments the encoded the trehalose biosynthetic pathway enzyme has at least 60% or at least 70% or at least 80% or at least 90% or at least 95% or at least 97%, or at least 98% amino acid sequence identity to SEQ ID NO: 2 (trehalose-6-phosphate synthase/phosphatase). In some embodiments the encoded trehalose biosynthetic pathway enzyme has at least 60% or at least 70% or at least 80% or at least 90% or at least 95% or at least 97% or at least 98% sequence identity to an amino acid sequence of at least 50 or at least 60 or at least 70 or at least 100 or at least 300 or at least 400 or at least 500 or at least 600 or at least 700 or at least 750 or at least 800 contiguous amino acids within any of SEQ ID NO: 2 or 4 or 5. In other embodiments the trehalose-6-phosphate synthase/phosphatase can be encoded by a nucleic acid sequence having at least 60% or at least 70% or at least 80% or at least 90% or at least 95% or at least 97% or at least 98% sequence identity to SEQ ID NO: 49.

In one embodiment the genetic modification inserts a stop codon into a coding sequence or regulatory sequence of one or more nucleic acid sequence(s) encoding a trehalose biosynthesis pathway enzyme to make a deletion or disruption of the gene. In one embodiment the genetic modification is a Glu723 to Val (E723V) mutation in the encoded polypeptide of SEQ ID NO: 2 (trehalose-6-phosphate synthase/phosphatase) or in a nucleic acid encoding a polypeptide having at least at least 60% or at least 70% or at least 80% or at least 90% or at least 95% or at least 98% sequence identity to SEQ ID NO: 2. Persons of ordinary skill will understand that a stop mutation or other mutation can be inserted at many other locations or loci within the nucleotide sequence, including in a promoter or other regulatory sequence of the gene, and achieve an attenuation of expression in the gene or in the activity of the encoded polypeptide. Such attenuation or other mutation can also cause a loss of function in the trehalose biosynthetic pathway enzyme and result in the effect of increase lipid productivity.

RNA Binding Domain

RNA binding proteins (RBPs) are involved in RNA metabolism. The function of RBPs is varied and may include transient binding to RNA sequences to assist with splicing, regulation of alternative splicing, a component of hnRNP proteins (heterogeneous nuclear ribonucleoprotein), processing, transport, or localization. Most RBPs have multiple RNA binding domains that include different types of RNA binding motifs that recognize RNA sequences or targets. The RNA recognition motif known as RRM is the most abundant RNA binding domain. In the invention the RNA binding domain can be an RRM from any one or more of the organisms described herein. In one embodiment the RNA binding domain can be an RRM superfamily protein, for example RRM_1. In other embodiments the RNA binding domain can be a protein from the PFAM 0076 family SEQ ID NO: 1 is the polypeptide sequence of an RNA binding domain with two RNA Recognition Motif (RRM) domains in the N-terminal half of the coding sequence. Orthologs are found in many green algae (Chlorophytes) and plants. The recombinant algal cell of the invention can have a genetic modification to a nucleotide sequence encoding an RNA binding domain that has at least 50% sequence identity or at least 60% sequence identity at least 70% sequence identity or at least 75% or at least 80% or at least 85% or at least 90% or at least 95% or at least 98% amino acid sequence identity with SEQ ID NO: 1, or with the RRM domain of SEQ ID NO: 3, or to a sequence of at least 100 or at least 150 or at least 200 or at least 250 or at least 300 contiguous amino acids within SEQ ID NO: 1 or SEQ ID NO: 3. In various embodiments the RNA binding domain is encoded by a nucleotide sequence having at least 60% sequence identity at least 70% sequence identity or at least 75% or at least 80% or at least 85% or at least 90% or at least 95% or at least 98% amino acid sequence identity with SEQ ID NO: 50.

In some embodiments nucleotide orthologs can encode an RRM domain having at least 70% sequence identity or at least 75% or at least 80% or at least 85% or at least 90% or at least 95% or at least 98% (and, optionally, in any of the embodiments less than 100%) amino acid sequence identity with SEQ ID NO: 1 or SEQ ID NO: 3.

In some embodiments the genetic modification to the nucleic acid sequence is an attenuation or a deletion, but in other embodiments can be an insertion, a point mutation, a disruption, or any of the genetic modifications described herein. In one embodiment the genetic modification inserts a stop codon into a nucleic acid sequence or gene encoding an RNA binding domain described herein, or into a nucleic acid sequence or gene encoding a trehalose biosynthesis enzyme described herein, or into a nucleic acid sequence or gene encoding an SGI1 polypeptide. In one embodiment the genetic modification is a Lys36 to stop mutation (L36Stop or L36*) inserted into a nucleic acid sequence encoding SEQ ID NO: 1 (or, for example, an L15* inserted into a nucleic acid sequence encoding SEQ ID NO: 3), or into a nucleic acid sequence or gene having at least at least 60% or at least 65% or at least 70% or at least 75% or at least 80% or at least 85% or at least 90% or at least 95% or at least 97% or at least 98% (and, optionally, less than 100% in any embodiment) sequence identity to SEQ ID NOs: 1 or 3 or, similarly, to a sequence encoding at least 100 or 150 or 200 or 250 or 300 contiguous amino acids of SEQ ID NOs: 1 or 3. The stop codon or other modification can also be made at many other loci or locations within a nucleic acid sequence or gene or regulatory sequence encoding an RNA binding domain or trehalose biosynthetic pathway enzyme, for example at a promoter, terminator, or other regulatory sequence. Such modifications can achieve an attenuation of expression in the gene or in the activity of the encoded polypeptide. Analogous modifications can be made to the sequence(s) for similar effect. Such attenuation or other mutation can also cause a loss of function in the RNA binding domain, trehalose biosynthetic pathway enzyme, or SGI1 polypeptide, and result in the effect of increase lipid productivity.

SGI1 Polypeptide

As described herein, SGI1 or "Significant Growth Improvement 1" polypeptide is a polypeptide that includes a Response Regulator receiver or "RR" domain (pfam PF00072) and a Myb-like binding domain, referred to herein simply as a "myb" domain (pfam PF00249), where the RR domain is positioned N-terminal to the myb domain or the myb domain is C-terminal to the RR domain The amino acid sequence of an SGI1 polypeptide that encompasses the RR domain and myb domain can include a stretch of amino acids that occurs between the RR and myb domains that may be poorly conserved or not conserved among SGI1 polypeptides. The amino acid sequence occurring between the RR domain and myb domain may be referred to herein as a linker between the two domains. The linker may be of any length, and in various examples may range in length from one to about 300 amino acids, from 10 to about 200 amino acids, or from 20 to about 150 amino acids in length. The linker region can optionally include a nuclear localization sequence (NLS).

An RR domain within an SGI1 protein can be characterized as pfam PF00072, or as a "signal receiver domain" or simply "receiver domain", and/or can be classified as cd00156 in the conserved domain database (CDD), as COG0784 in the Clusters of Orthologous Groups of proteins database, or as an Interpro "CheY-like superfamily" domain, IPR011006. The RR domain is found in bacterial two-component regulatory systems (like the bacterial chemotaxis two-component system that includes a polypeptide known as CheY), in which it receives a signal from a sensor partner. The RR domain of such systems is often found N-terminal to a DNA binding domain and can include a phosphoacceptor site. Alignment of the RR domains of algal SGI1 attenuation mutant strains can be shown. Sub-sequences of the RR domain from *Parachlorella* sp. WT-1185, *Coccomyxa subellipsoidea*, *Ostreococcus lucimarinus*, *Chlamydomonas reinhardtii*, *Chromochloris zofingiensis*, *Volvox carteri*, *Tetraselmis* sp. 105, *Oocystis* sp. WT-4183, and *Micromonas* sp. RCC299 show substantial homology.

A myb domain within an SGI1 protein can be characterized, for example, as pfamPF00249: "Myb-like DNA-binding domain", and/or may be identified as conserved domain TIGR01557 "myb-like DNA-binding domain, SHAQKYF class", or as an Interpro Homeobox-like domain superfamily domain (IPR009057) and/or an Interpro Myb domain (IPRO1 7930). Alignment and substantial homology was also shown of the Myb domains of algal SGI1-KO strains. Shown are sub-sequences of the Myb domains from *Parachlorella* sp. WT-1185, *Coccomyxa subellipsoidea*, *Ostreococcus lucimarinus*, *Chlamydomonas reinhardtii*, *Chromochloris zofingiensis*, *Volvox carteri*, *Tetraselmis* sp. 105, *Oocystis* sp. WT-4183, and *Micromonas* sp. RCC299.

In addition to having an RR domain N-terminal to a myb domain, an SGI1 protein as provided herein can have a score of 300 or higher, 320 or higher, 340 or higher, 350 or higher, 360 or higher, or 370 or higher with an e-value of less than about 1e-10, 1e-50, 1e-70, or 1e-100, when scanned with a Hidden Markov Model (HMM) designed to score proteins on the basis of how well a protein's amino acid sequence matches the conserved amino acids of a region of SGI1 homologs in algae. The region of SGI1 polypeptides used to develop the HMM is the amino acid sequence that includes (proceeding in the N-terminal to C-terminal direction) the RR domain, the linker, and the myb domain In a HMM, highly conserved amino acid positions are weighted more heavily than poorly conserved amino acid positions within a compared region of the polypeptides to arrive at the score. Polypeptides having scores of at least about 300, or of 350 or greater, such as for example 370 or greater, when scanned with an HMM model based on protein sequences of algal SGI1 polypeptides that include a single continuous sequence that includes the RR domain, linker, and myb domain developed using include, without limitation, polypeptides of the algal and plant species *Parachlorella* sp. 1185 (SEQ ID NO:8), *Coccomyxa subellipsoidea* (SEQ ID NO:9), *Ostreococcus lucimarinus* (SEQ ID NO:10), *Chlamydomonas reinhardtii* (SEQ ID NO:11), *Chromochloris zofingiensis* (SEQ ID NO: 12), *Volvox carteri* (SEQ ID NO:13), *Tetraselmis* sp. 105 (SEQ ID NOs: 14-16, *Oocystis* sp. (SEQ ID NO:17), *Micromonas* sp. RCC299 (SEQ ID NO:18), and *Micromonas pusilla* (SEQ ID NO:19), *Sphagnumfallax* (SEQ ID NO:20), and *Physcomitrella* patens (SEQ ID NO:21). Additional SGI1 orthologs from additional algae species are identifiable by persons of ordinary skill in the art.

The SGI1 polypeptide encoded by a nucleic acid comprised by the recombinant algal or plant cells of the invention can have at least 50%, at least 55%, at least 60%, at least 65%, at least 70%, at least 75%, at least 80%, at least 85%, at least 90%, at least 95%, at least 96%, at least 97%, at least 98%, or at least 99% (and, optionally, in any embodiment less than 100%) amino acid sequence identity to any SGI1 polypeptide sequence of SEQ ID NOs: 6-21, or to fragments of any of them comprising a consecutive sequence of at least 100, or at least 125, or at least 150, or 200 or more amino acid residues of the entire protein where the polypeptide has an RR domain and a myb domain, and the RR domain can be N-terminal to the myb domain, where the SGI1 polypeptide is a naturally occurring polypeptide or a variant thereof. In various embodiments, the SGI1 polypeptide is from a plant or algal species, i.e., is a naturally-occurring polypeptide of a plant or algal species. A gene or nucleotide sequence encoding an SGI1 polypeptide as provided herein, for example a gene that is disrupted or whose expression is attenuated in a mutant as provided herein, can be a naturally-occurring gene of a plant or algal species that encodes a polypeptide as disclosed herein.

In various embodiments the encoded SGI1 polypeptide can have a (Myb domain) amino acid sub-sequence having at least 75% or at least 80% or at least 85% or at least 90% or at least 95% or at least 98% (and, optionally, in any embodiment less than 100%) sequence identity to a Myb domain sequence of any of SEQ ID NO: 22-30, or to a consecutive sequence of at least 25, or at least 30, or at least 50 or at least 75 amino acid residues of the entire sequence. In various embodiments any of these myb domains can be present in an SGI1 polypeptide with any of the RR domains described herein (e.g., SEQ ID NO: 31-48).

An SGI1 gene that encodes a polypeptide having the sequence of a naturally-occurring algal SGI polypeptide can be a gene having a naturally-occurring gene sequence, or can have a sequence that varies from the sequence of a naturally-occurring gene. In various embodiments, an SGI1 gene that is attenuated, mutated, or disrupted in a mutant photosynthetic organism as disclosed herein can be a gene that is identified through homology searching, for example, using one or more sequences disclosed herein as queries, and/or by HMM scanning, where the HMM is built from amino acid sequences, for example upon multiple alignment of at least six SGI1 polypeptides, where the amino acid sequences include an RR domain and a myb domain, where the RR domain is N-terminal to the myb domain, and where there is a linker sequence between the RR and myb domains that does not belong to either domain In some embodiments, an SGI1 polypeptide can be the sequence of an algal or plant SGI1 polypeptide, or is a variant of a naturally-occurring algal or plant SGI1 polypeptide, and can contain a Response Regulator receiver domain as a sub-sequence, for example a sub-sequence of any of SEQ ID NO: 6-21, which can be a consecutive sequence of at least 25, or at least 30, or at least 50 or at least 75 amino acid residues of the entire sequence. The Response Regulator receive domain can contain an amino acid sub-sequence having at least 50%, at least 55%, at least 60%, at least 65%, at least 70%, at least 75%, at least 80%, at least 85%, at least 90%, at least 95%, at least 96%, at least 97%, at least 98%, or at least 99% (and, optionally, in any embodiment less than 100%) sequence identity to any one of the Response Regulator receiver domains of SEQ ID NO: 31-48, or to a consecutive sequence of at least 25, or at least 30, or at least 50 or at least 75 amino acid residues of the entire sequence.

Persons of ordinary skill know how to calculate the percent of "sequence identity" between two sequences. In one embodiment the percent of sequence identity can be determined by BLAST (Basic Local Alignment Search Tool) analysis using the algorithm employed by the programs blastp, blastn, blastx, tblastn, and tblastx (Altschul (1997), Nucleic Acids Res. 25, 3389-3402, and Karlin (1990), Proc. Natl. Acad. Sci. USA 87, 2264-2268). In one embodiment the search parameters for histogram, descriptions, alignments, expect (i.e., the statistical significance threshold for reporting matches against database sequences), cutoff, matrix, and filter (low complexity) can be at the default settings. The default scoring matrix used by blastp, blastx, tblastn, and tblastx can be the BLOSUM62 matrix (Henikoff (1992), Proc. Natl. Acad. Sci. USA 89, 10915-10919). For blastn the scoring matrix can be set by the ratios of M (i.e., the reward score for a pair of matching residues) to N (i.e., the penalty score for mismatching residues), wherein the default values for M and N can be +5 and −4, respectively. Four blastn parameters can be adjusted as follows: Q=10 (gap creation penalty); R=10 (gap extension penalty); wink=1 (generates word hits at every winkth position along the query); and gapw=16 (sets the window width within which gapped alignments are generated). The equivalent Blastp parameter settings for comparison of amino acid sequences can be: Q=9; R=2; wink=1; and gapw=32. A Bestfit comparison between sequences, available in the GCG package version 10.0, can use DNA parameters GAP=50 (gap creation penalty) and LEN=3 (gap extension penalty), and the equivalent settings in protein comparisons can be GAP=8 and LEN=2.

Recombinant Alga

The recombinant mutant algae of the invention demonstrate a significant increase in the production of lipid in the organism, which can be measured (for example) using fatty acid methyl esters (FAME) analysis. The increase in lipid production can be measured as an increase in total FAME produced by the organisms. The recombinant cells of the invention having a genetic modification to a nucleic acid sequence or gene encoding a trehalose biosynthesis pathway enzyme disclosed herein and/or a genetic modification to a nucleic acid sequence encoding an RNA binding domain disclosed herein and, optionally for any of them, a genetic modification to a nucleic acid sequence encoding an SGI1 polypeptide disclosed herein, can exhibit at least 50% or at least 60% or at least 70% or at least 80% or at least 90% or at least 100% greater lipid productivity compared to a corresponding control alga. In other embodiments the increase in lipid productivity can be 15-35% or 15-40% or 25-45% or 15-50% or 25-70% or 25-90% or 25-100% or 25-150% or 25-200%. In one embodiment lipid productivity is measured using total fatty acid methyl ester assay (FAME) known to persons of ordinary skill in the art.

In another embodiment the recombinant cells of the invention having the genetic modification to one or more trehalose biosynthesis pathway enzyme(s) and/or a genetic modification to one or more RNA binding domain(s) and, optionally for any of them, a genetic modification to one or more nucleic acid sequence(s) encoding SGI1 polypeptide, exhibit at least 50% or at least 60% or at least 70% or at least 80% or at least 90% or at least 100% or at least 150% or at least 200% greater biomass productivity versus a control alga. In other embodiments the increase in biomass productivity can be 15-35% or 15-40% or 25-45% or 15-50% or 25-70% or 50-100% or 50-200%. In one embodiment the biomass productivity can be measured as total organic carbon (TOC) using assays known to persons of ordinary skill in the art.

The recombinant cells or organisms of the invention can have the disclosed higher amounts of lipid productivity and/or the higher disclosed amounts of biomass productivity.

Increased Lipid Productivity

Any of the recombinant algal cells disclosed herein can exhibit increased lipid productivity. For example, recombinant algal cells having a genetic modification to one or more nucleic acid sequence(s) encoding a trehalose biosynthetic enzyme (e.g., trehalose-6-phosphate synthase/phosphatase) and/or to one or more nucleic acid sequence(s) encoding an RNA binding domain and, optionally with either or both of them, a genetic modification to one or more nucleic acid sequence(s) encoding SGI1 polypeptide, exhibit higher lipid productivity.

In any embodiment lipid productivity can be measured using the fatty acid methyl ester (FAME) profile, which is known to persons of ordinary skill in the art. In various embodiments any of the recombinant algal cells or organisms of the invention can produce at least 20% more or at least 25% more or at least 30% more or at least 35% more, or at least 50% more or at least 60% more or at least 70% more or at least 80% more or at least 90% more or at least 100% more or at least 125% more or at least 150% more or at least 200% more lipid product than a corresponding (control) cell or organism. In one embodiment the lipid productivity can be measured using the FAME profile of the respective cells or organisms.

An increase in lipid production or lipid productivity can also be measured in grams per square meter per day of the surface of a cultivation vessel (e.g., a flask, photobioreactor, cultivation pond). In various embodiments the recombinant alga of the invention produce at least 3 or at least 4 or at least 5 or at least 6 or at least 7 grams per square meter per day of lipid, which can be measured by the FAME profile. In any of the embodiments the high lipid and/or high biomass productivity phenotype can be obtained under nitrogen deplete conditions, which can be with semi-continuous dilutions (e.g., dilution by about 30% or by about 40% or by about 50%, once per day, and replacing with fresh medium). In one embodiment the lipid product is a fatty acid and/or derivative of a fatty acid. In one embodiment the fatty acids and/or derivatives of fatty acid comprise one or more species of molecules having a carbon chain between C8-C18 or C8-C20 or C8-C22 or C8-C24.

In any of the embodiments the genetic modification to a gene or nucleic acid sequence encoding a RBD domain described herein and/or a gene or nucleic acid sequence encoding a trehalose biosynthetic pathway enzyme described herein, and optionally with either or both of them, a genetic modification to a nucleic acid sequence encoding an SGI1 polypeptide described herein, can result in an attenuation of expression of the respective genes. The genetic modification of any one or more of these genes or nucleic acid sequences can be a knockout, a targeted mutation and gene replacement, a gene replacement, a promoter replacement, a deletion, an insertion, a substitution, a functional deletion, a disruption in a gene or in its regulatory sequence, as well as the introduction of transgenes into the organism.

Biomass Productivity

The recombinant algal cells of the invention can also have higher biomass productivity than a corresponding organism not having a genetic modification to the gene or nucleic acid sequence encoding one or more trehalose biosynthetic pathway enzyme(s) described herein and/or to one or more gene(s) or nucleic acid sequence(s) encoding an RBD domain described herein and, optionally with either or both of them, a genetic modification to a gene or nucleic acid sequence encoding one or more SGI1 polypeptide(s) described herein. Biomass can be measured using the total organic carbon (TOC) analysis, known to persons of ordinary skill in the art. The recombinant cells can have at least 20% higher or at least 25% higher or at least 30% higher or at least 35% higher, or at least 50% higher or at least 60% higher or at least 70% higher or at least 80% higher or at least 90% higher or at least 100% higher or at least 125% higher or at least 150% higher or at least 200% higher biomass productivity than a corresponding (control) cell or organism, which can be measured by total organic carbon analysis. Biomass productivity can be measured as mg/ml of culture per time period (e.g., 1 day or 2 days or 3 days or 4 days or 5 days).

In any of the embodiments the recombinant alga can have the amounts of higher biomass productivity and/or higher lipid productivity stated herein under nitrogen deplete conditions. Thus, in one embodiment the recombinant alga of the invention can have higher total organic carbon production than a corresponding (control) cell or organism, which higher amount can be produced under nitrogen deplete or low nitrogen conditions. In one embodiment biomass productivity can be evaluated by measuring an increase in the total organic carbon of the cells.

Methods of Producing Lipid

The invention also provides methods for producing a composition containing lipids. The methods involve subjecting a culture of algal organisms described herein to at least one treatment of uv radiation (or gamma radiation, or both) to produce a recombinant algal organism described herein, cultivating the recombinant algal organisms in a suitable medium (such as any described herein), and thereby producing a composition containing lipids. Optionally the lipids can be isolated from the recombinant algal organisms. The recombinant alga can be cultivated in any suitable media, such as any of those described herein. The uv treatment can involve, for example, subjecting the culture to uv light (or gamma radiation, or both) for a suitable period of time or under a suitable uv regimen. The recombinant alga can be cultivated for at least 2 days or at least 3 days, or at least 4 days, or at least 5 days, or at least 6 days, or at least 10 days, or at least 20 days, or from 2-10 days, or from 2-20 days or from 2-25 days.

Any of the recombinant cells or organisms of the invention can be cultivated in batch, semi-continuous, or continuous culture. In some embodiments the culture medium can be nutrient replete, or nitrogen deplete (—N). In some embodiment the culturing is under photoautotrophic conditions, and inorganic carbon (e.g., carbon dioxide or carbonate) can be the sole or substantially the sole carbon source in the culture medium. Nitrogen deplete conditions can be achieved by utilizing a culture medium that has no significant source of nitrogen available for cell growth. In various embodiments nitrogen deplete conditions can involve culturing in a buffer having less than 0.5 mM of nitrogen in any available form external to the cell or organism. In some embodiments the cells can be cultured in 0.5 mM or less of KNO3 or urea as a nitrogen source.

The invention also provides methods of producing a biofuel involving cultivating a recombinant algal organism described herein. The methods can also include a step of harvesting a biofuel from a recombinant algal organism of the invention. The recombinant organism can be cultivated in any growth medium, such as any described herein. In one embodiment the recombinant organism is cultivated in a nitrogen deplete medium. In various embodiments the cultivating can occur for a period of at least 3 days or at least 5 days or at least 7 days or at least 15 days or at least 20 days.

FAME and TOC Analysis Methods

The lipid productivity of the cells or organisms can be measured by any method accepted in the art, for example as an increase or decrease in fatty acid methyl esters (FAME) comprised in the cell, i.e., analysis of the cell or organism's FAME profile. In some embodiments any of the recombinant algal cells or organisms of the invention can have higher biomass productivity versus corresponding control cells or organisms. In some embodiments any of the recombinant algal cells or organisms of the invention can have both higher lipid productivity and higher biomass productivity compared to a corresponding control cell or organism. Biomass productivity can be measured by any methods accepted in the art, for example by measuring the total organic carbon (TOC) content of a cell. Embodiments of both methods are provided in the Examples.

"FAME lipids" or "FAME" refers to lipids having acyl moieties that can be derivatized to fatty acid methyl esters, such as, for example, monoacylglycerides, diacylglycerides, triacylglycerides, wax esters, and membrane lipids such as phospholipids, galactolipids, etc. In some embodiments lipid productivity is assessed as FAME productivity in milligrams per liter (mg/L), and for algae, may be reported as grams per square meter per day (g/m2/day). In semi-continuous assays, mg/L values are converted to g/m2/day by taking into account the area of incident irradiance (the SCPA flask rack aperture of 1½ inches×33/8", or 0.003145 m2) and the volume of the culture (550 ml). To obtain productivity values in g/m2/day, mg/L values are multiplied by the daily dilution rate (30%) and a conversion factor of 0.175. Where lipid or subcategories thereof (for example, TAG or FAME) are referred to as a percentage, the percentage is a weight percent unless indicated otherwise. The term "fatty acid product" includes free fatty acids, mono-di, or tri-glycerides, fatty aldehydes, fatty alcohols, fatty acid esters (including, but not limited to, wax esters); and hydrocarbons, including, but not limited to, alkanes and alkenes).

EXAMPLES

Example 1

Production of SGI1 Mutants

The production of algal strains containing a genetic modification in a nucleic acid sequence encoding an SGI1 polypeptide is known in the art and is detailed in US 2018/0186842, published Jul. 5, 2018, and which is hereby incorporated by reference in its entirety, including all tables, figures, and claims.

Briefly, wild-type Parachlorella sp. (a Chlorophyte, or green algae species) obtained from marine environments were mutagenized with uv radiation in a STRATALINKER® 2400 uv crosslinker (Agilent Technologies, Santa Clara, CA) and selected based on low chlorophyll fluorescence after low light acclimation.

The cells were grown to mid-log phase and then diluted to $1\times10^6$ (1e6) cells/mL with a nutrient replete growth medium. The cell suspensions were transferred to a Petri dish and placed within a STRATALINKER® 2400 UV crosslinker (Agilent Technologies, Santa Clara, CA) with the plate lid removed. UV irradiation was carried out with 10,000, 25,000, and 50,000 µJ/cm2. After irradiation, cell suspensions were pipetted into a shake flask wrapped in foil to prevent light exposure for twenty-four hours during recovery. Following mutagenesis and recovery cells from pale colored colonies were selected and allowed to grow from between one and five days in low (100 µmol photons m-2 sec-1) light, after which they were sorted by flow cytometry to select cells having low chlorophyll fluorescence.

Further primary screening of antenna-reduced lines isolated through flow cytometry was conducted through the selection of pale green or yellow colonies visually after sorted cells were plated. In order to screen putative antenna-reduced lines from other reduced pigment mutants and false positives, selected colonies were subjected to a medium-throughput secondary cultivation screen to acclimate the isolates to low light conditions prior to photo-physiological measurements. Chlorophyll fluorescence was monitored during low light acclimation to select colonies that retained the reduced chlorophyll fluorescence characteristic of the high light acclimated state. Clones that were selected demonstrated only small increases in chlorophyll (relative to wild type cells) when transferred from high to low light.

Semi-continuous culture assays in constant high light (approximately 1,700 µmol photons m-2 sec-1) using 165 ml cultures in 75 cm2 tissue culture flasks were performed to identify strains having increased productivity (increased rate of biomass production, measured as TOC accumulation) with respect to the wild type progenitor. Two 75 cm2 flasks were inoculated with seed culture of a given mutant strain with CO2-enriched air (1% CO2) bubbled through the cultures. Samples for TOC analysis were taken from the culture removed for the dilution. Isolates were identified having increased productivity.

Genome sequencing and genotyping of resultant strains revealed mutations including distinct SNPs. The effect of higher biomass productivity was found to be related to an SNP in the sequence of SGI1 polypeptide at amino acid 250, which was changed from Leu to Pro (i.e., a Leu250Pro SNP). The gene encoding SGI1 polypeptide in Parachlorella sp. has the nucleotide sequence of SEQ ID NO: 6, and the coding sequence of SEQ ID NO: 7, which encodes the amino acid sequence of SEQ ID NO: 8. The SNP was found to result in a Leu250Pro mutation in SGI1 polypeptide. This mutation was recapitulated in a wild-type Cas9 editor strain of Parachlorella sp. to produce "SGI1 mutants," and these cells were then used in subsequent procedures.

Example 2

Mutagenesis

The SGI1 mutants from Example 1 were irradiated with uv light in a STRATALINKER® 2400 uv crosslinker (Agilent Technologies®, Santa Clara, CA). Irradiation was done in four dosages with duplicates per dosage. Cells were diluted to a concentration of $5\times10^6$ (5e6) cells/ml and irradiated on agar plates with approximately $5\times10^7$ (5e7) cells total per petri dish. Irradiation dosages included 16 seconds at 27,000 uJ/cm$^2$, 12 seconds at 20,000×uJ/cm$^2$, 8 seconds at 13,000 uJ/cm$^2$, and 6 seconds at 10,000 uJ/cm$^2$.

Example 3

Growth and Bodipy Staining

Mutagenized cells were then grown to a suitable concentration as measured by OD730 of 3.0 in flasks containing PM074 media. Cells were then transferred to media containing PM123 media (aquarium salts, PROLINE A®, and PROLINE B® (Pentair Aquatic Eco-Systems®, Inc.)) and a final OD730 of 0.1 (PROLINE A® and PROLINE B® together include 8.8 mM NaNO3, 0.361 mM NaH2PO4·H2O, 10× F/2 Trace metals, and 10× F/2 Vitamins (Guillard (1975) "Culture of phytoplankton for feeding marine invertebrates," eds. Smith, W. L. and Chanley, M. H., Plenum Presse, New York, pp. 26-60). After growing to suitable concentration (OD730 of 2.8) cells were spun down in a centrifuge and re-suspended in flasks containing nitrogen-free PM67 media (aquarium salts, K2HPO4, vitamin mix, chelated trace metal mix). Cells were placed in a glass tank flask and a final concentration of cells of OD730 of 1.4 was reached and cells were placed under a constant stream of 1% CO2 in air.

After 48 hours of batch growth in nitrogen deplete media (i.e., the culture medium had no nitrogen source) an aliquot of cells was removed and subjected to staining with the lipid-specific dye BODIPY (boron-dipyrromethene). Mutant cells with the highest level of BODIPY staining were enriched by fluorescence activated cell sorting (FACS). Enriched cell populations were grown and re-inoculated and allowed to grow as above, and again subjected BODIPY staining and FACS at 48 h under nitrogen deplete (—N) batch growth. This iterative process was repeated for a total of five rounds of sorting, with the final sort resulting in single cell isolates.

Example 4

Fame and TOC Analysis

Figure 1B:
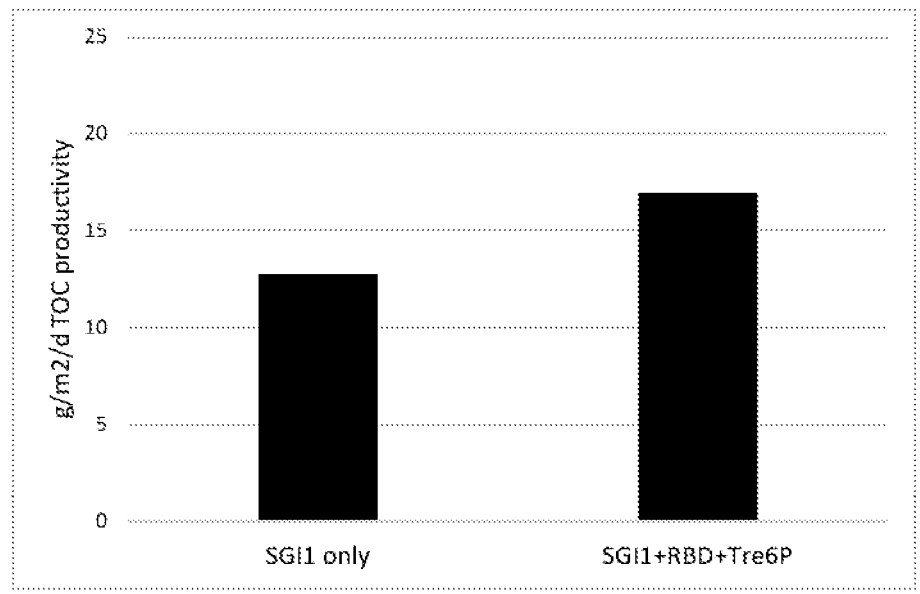

Once rendered axenic from bacterial contamination by treatment of cultures with streptomycin at 0.6 mg/ml, isolates having the SGI1 mutation plus the RNA binding domain (RBD) and trehalose-6-phosphate synthase/phosphatase (Tre6P) attenuations were cultivated under nitrogen-deplete growth conditions and compared to the parental SGI1-KO only mutant strain for nitrogen-deplete batch lipid and biomass productivity. The FAME and TOC measurements show the amount of fixed carbon that is partitioned to lipids and nitrogen-deplete lipid productivity. FIG. 1a shows that the isolates exhibited an increase in FAME/TOC ratio (an indicator of how much fixed carbon is partitioned to lipids) compared to the SGI1-KO only mutants, and FIG. 1b shows higher TOC productivity. Thus, mutants having the SGI1+RBD+Tre6P attenuations were isolated and had improved lipid productivity versus mutants having the SGI1-KO alone.

Total organic carbon (TOC) of the algal culture samples was determined by diluting 2 mL of cell culture to a total volume of 20 mL with DI water. Three injections per measurement were injected into a TOC high sensitivity analyzer for determination of Total Carbon (TC) and Total Inorganic Carbon (TIC). The combustion furnace was set to 720° C., and TOC was determined by subtracting TIC from TC. The 4-point calibration range was from 2 ppm to 200 ppm corresponding to 20-2000 ppm for non-diluted cultures with a correlation coefficient of $r^2$ (r squared) greater than 0.999.

To determine lipid content, FAME analysis was performed on 2 mL samples that were dried using an evaporator. To the dried pellets the following was added: 500 µL of 500 mM KOH in methanol, 200 µL of tetrahydrofuran containing 0.05% butylated hydroxyl toluene, 40 µL of a 2 mg/ml C11:0 free fatty acid/C13:0 triglyceride/C23:0 fatty acid methyl ester internal standard mix and 500 µL of glass beads (425-600 um diameter). The vials were capped with open top PTFE septa-lined caps and placed in a tissue homogenizer at 1.65 krpm for 7.5 minutes. The samples were then heated at 80° C. for five minutes and allowed to cool. For derivatization, 500 µL of 10% boron trifluoride in methanol was added to the samples prior to heating at 80° C. for 30 minutes. The tubes were allowed to cool prior to adding 2 mL of heptane and 500 µL of 5 M NaCl. The samples were then vortexed for five minutes at 2 krpm and finally centrifuged for three minutes at 1 krpm. The heptane layer was sampled using an autosampler. Quantitation used the 80 µg of C23:0 FAME internal standard.

Example 5

Genotyping of Mutants

Genomic DNA was isolated from these mutants and from the SGI1 only mutant parental strain (STR0012) and the wild-type corresponding control strain (STR0010). Isolated gDNA was sequenced using Next Generation sequencing on an Illumina® instrument (Illumina, Inc., San Diego, CA). Sequence reads were processed, mapped to the wild type reference genome and analyzed by a small variants caller algorithm (derived from the FreeBayes polymorphism detection software, which is a Bayesian genetic variant detector designed to find small polymorphisms, specifically SNPs, indels (insertions and deletions), MNPs (multi-nucleotide polymorphisms), and complex events (composite insertion and substitution events) smaller than the length of a short-read sequencing alignment. Analysis of small nucleotide polymorphisms (SNPs) and small insertions/deletions (InDels) revealed the sequenced strains to be genetic siblings of each other having a core set of 28 polymorphisms shared across the strains.

The SNPs shown in Table 1 revealed the candidate genes where the underlying causative mutations causing the high lipid phenotype might occur. Fifteen SNPs were either intergenic or present in introns of a gene; assessment of transcriptomics and RNA sequence data from the new mutants indicated that these SNPs had no impact on neighboring gene expression or intron splicing.

But thirteen of the 28 SNPs were prioritized for genetic recapitulation based on the deduced change in coding sequence of the encoded gene. One of the 13 sibling high lipid mutants, named Strain 600 (STR0600), was selected for all further experiments. The 13 mutants were identified as noted in Table 1.

TABLE 1

| | | | | |
|---|---|---|---|---|
| Downstream gene variant | Haloacid dehalogenase-like hydrolase domain-containing protein 2 | SNP | G | A |
| Downstream gene variant | Conserved predicted protein | MNP | GG | AA |

TABLE 1-continued

| | | | | |
|---|---|---|---|---|
| Downstream gene variant | Glucuronoxylan 4-O-methyltransferase 1 | SNP | C | T |
| Intron variant | SNF2 domain-containing protein/helicase domain-containing protein/F-box family protein isoform 3 | SNP | T | C |
| Intron variant | Amino acid transmembrane transporter | SNP | C | T |
| Intron variant | AarF domain-containing kinase | SNP | G | A |
| Upstream gene variant | Conserved predicted protein | SNP | T | A |
| Upstream gene variant | Conserved predicted protein | Deletion | CTCATCAC | CTCAC |
| Upstream gene variant | Zinc finger ccch domain-containing protein 29 | SNP | G | A |
| Upstream gene variant | D-amino acid aminotransferase | SNP | T | A |
| Intron variant | Exostosin family protein isoform 1 | SNP | C | A |
| Upstream gene variant | Conserved predicted protein | SNP | T | G |
| Intron variant | Exostosin family protein isoform 1 | Insertion | ATT | ATTT |

Example 6

Genetic Recapitulation

To determine the mutation(s) that are the cause of the high lipid phenotype, knockouts, and/or exact recapitulation of SNPs observed in STR0600 were re-created in a markerless Cas9/Cre expression strain containing a SGI1 knockout (SGI1-KO). In addition, a variant of STR00600 in which Cas9/Cre expression cassettes were integrated in a markerless fashion was generated in order to examine the effect of reverting SNPs back to wild type. Thus individual SNPs could be evaluated to determine which were necessary to produce the high lipid phenotype, and whether the phenotype might have a complex genetic underpinning where one SNP is not sufficient to recapitulate the phenotype.

All strains generated were tested for the high lipid and/or high biomass productivity phenotype under nitrogen deplete (—N) batch conditions in a simplified assay conducted in T25 flasks containing PM153 buffer for an OD730 of 0.1. PM153 is a nutrient replete medium that is based on PM074 but includes urea instead of nitrate as the nitrogen source. It is made by adding 1.3 ml Proline® F/2 Algae Feed Part A (Pentair Aquatic Eco-Systems) and 1.3 ml 'Solution C' to a final volume of 1 liter of a solution of aquarium salts (17.5 g/L), and then adding 4 ml if 1.1 M filter-sterilized urea. Solution C is 38.75 g/L NaH2PO4 H2O, 758 mg/L thiamine HCl, 3.88 mg/L vitamin B12, and 3.84 mg/L biotin.

PM074 is a nutrient replete medium. While any suitable algal growth medium can be employed in the invention, PM074 is made by adding 1.3 ml Proline® F/2 Algae Feed Part A (Pentair Aquatic Eco-Systems, Inc., Apopka, FL) and 1.3 ml Proline® F/2 Algae Feed Part B to a final volume of 1 liter of a solution of Instant Ocean salts (35 g/L) (Pentair Aquatic Eco-Systems Inc., Apopka, FL). Proline A® and Proline B® together include 8.8 mM NaNO3, 0.361 mM NaH2PO4·H2O, 10× F/2 Trace metals, and 10× F/2 Vitamins (Guillard (1975) *Culture of phytoplankton for feeding marine invertebrates* in "Culture of Marine Invertebrate Animals." (eds: Smith W. L. and Chanley M. H.) Plenum Press, New York, USA. pp 26-60).

For biomass and lipid productivities, strains were pre-acclimated in a 14:10 diel 1% CO2 incubator and scaled to 1000 ml in PM153 media. Cultures were normalized to about 350 mg/l TOC, which is 60% of the empirically determined steady state standing biomass density for a daily 40% dilution rate. The total culture volume was 420 ml in a 500 ml square polycarbonate bottle. Flasks were kept at 30° C. using a water bath, stirred via magnetic bar and 1% CO2 bubbled at 300 ml/min. Light was supplied by LED panels through a 0.0875 m2 aperture and programmed to a 14:10 diel cycle. For nitrogen replete biomass productivity measurements, samples were taken for OD730, Flow Cytometry, FAME and TOC analysis at dusk and the cultures diluted back 40% with PM153 in a semi-continuous manner for 8-9 days. Following the nitrogen replete semi-continuous mode, the flask was removed at dusk, pelleted and the supernatant discarded. The strains were resuspended in PM152 (nitrogen-deplete) media and normalized to about 250 mg/l TOC as empirically determined to give maximal lipid productivity. The cultures were placed back into new 500 ml bottles at 420 ml volume as above. The cultures were grown in batch mode to test lipid productivity during nitrogen deplete induction with sampling again at dusk.

Figure 2A:
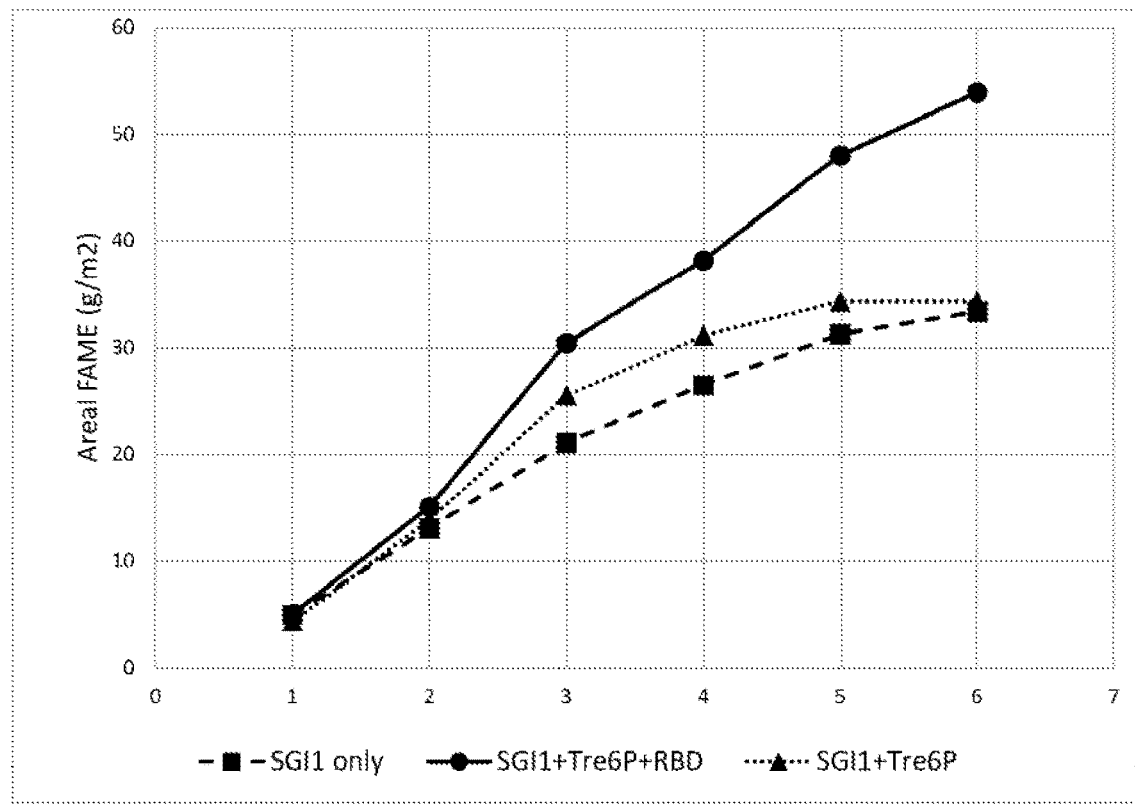
FIGS. 2A-2C, in FIG. 2A the Tre6P recapitulation (SGI1+ Tre6P) showed increased areal FAME productivity over the SGI1-KO strain (SGI1 "knock out" only) in the early stages of nitrogen starvation. By Day 6 levels fall to the same level as the SGI1-KO strain.
Figure 2B:
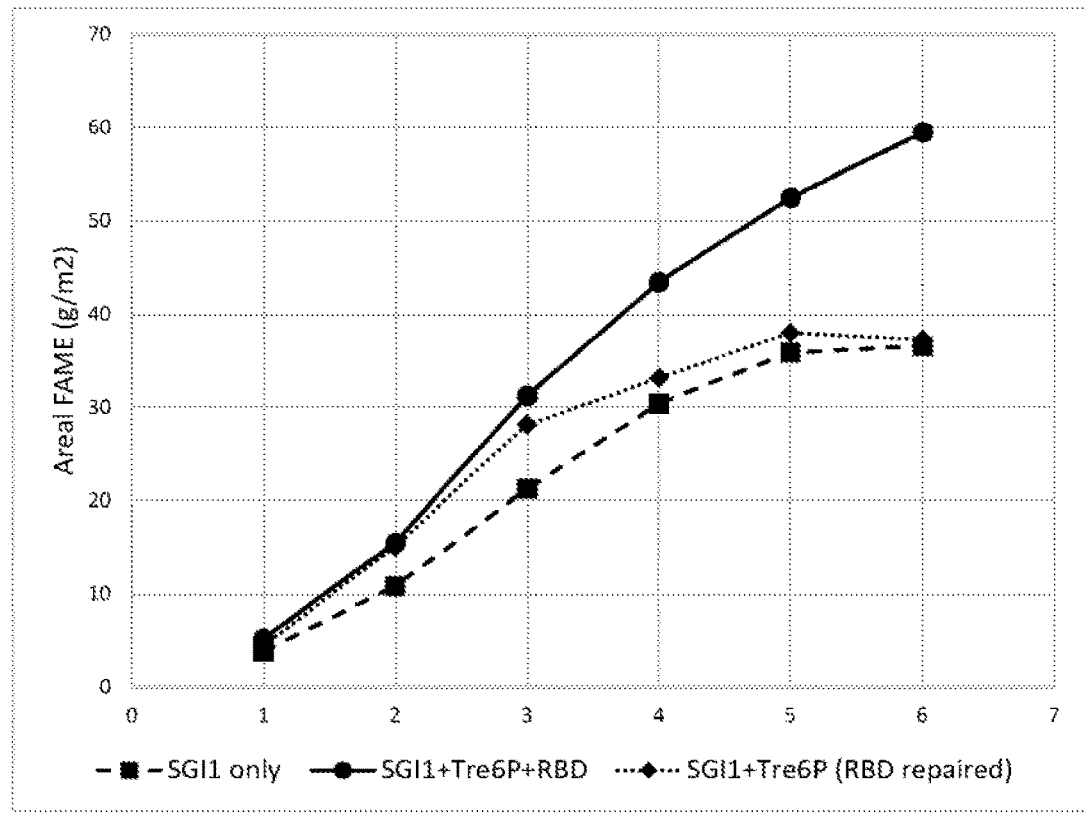
Figure 2C:
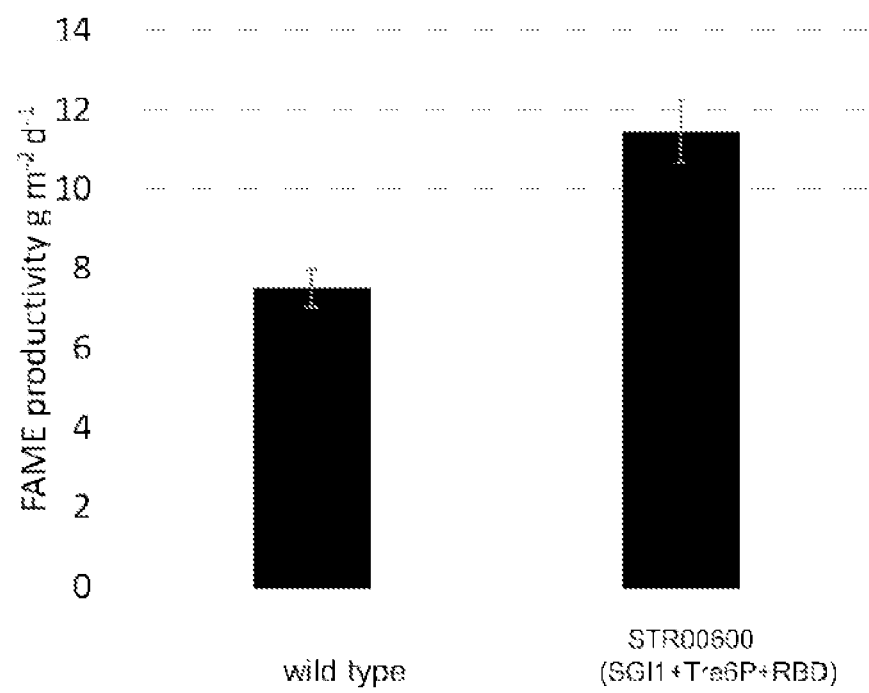
Figure 3A:
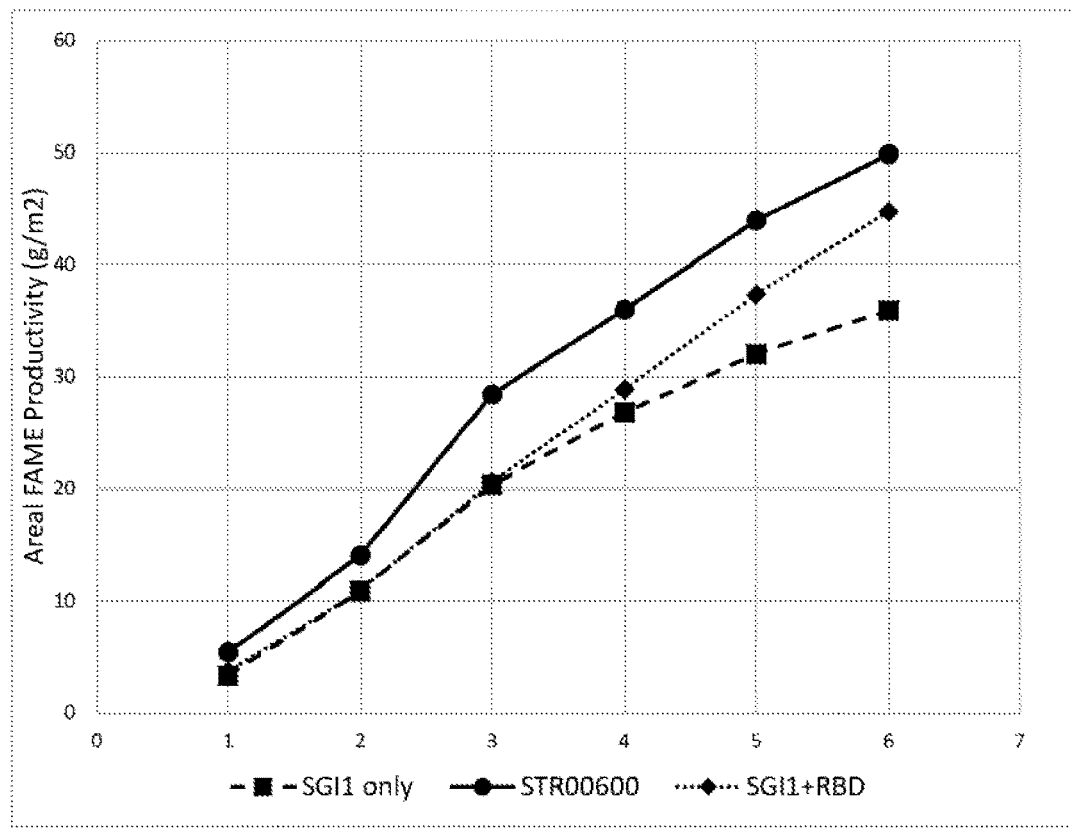
FIGS. 3A-3B shows late improvements in lipid productivity driven by the RBD deletion.
Figure 3B:
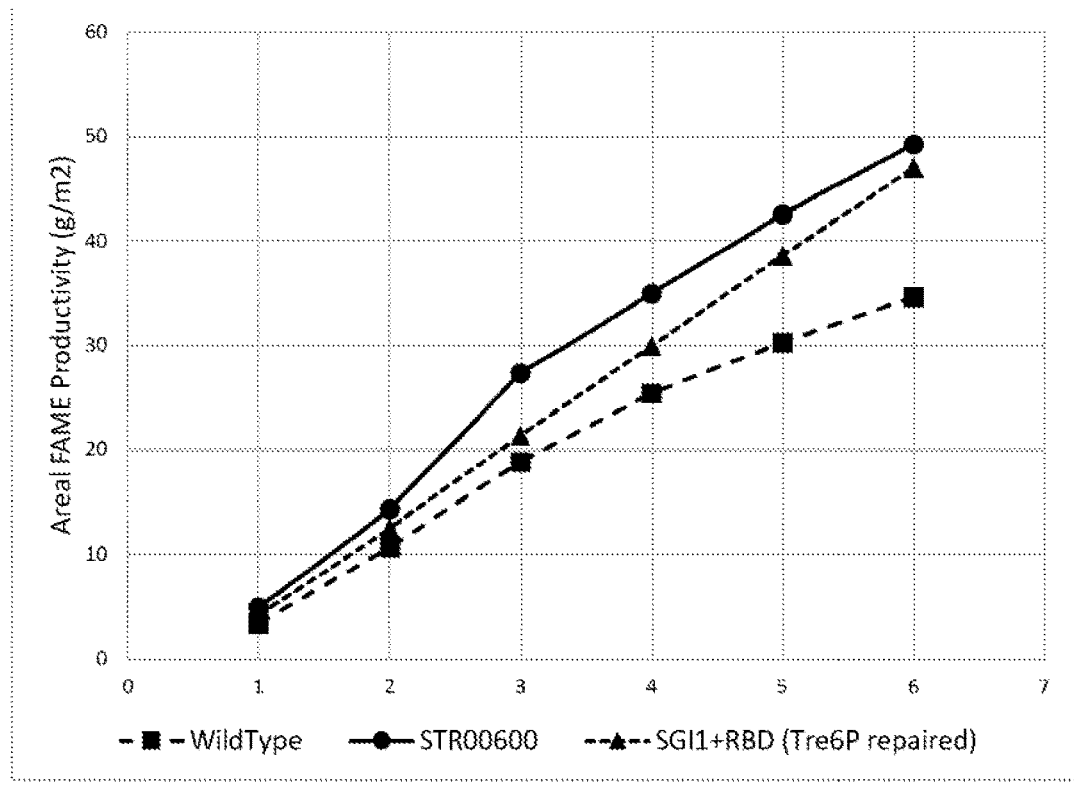
Figure 5A:
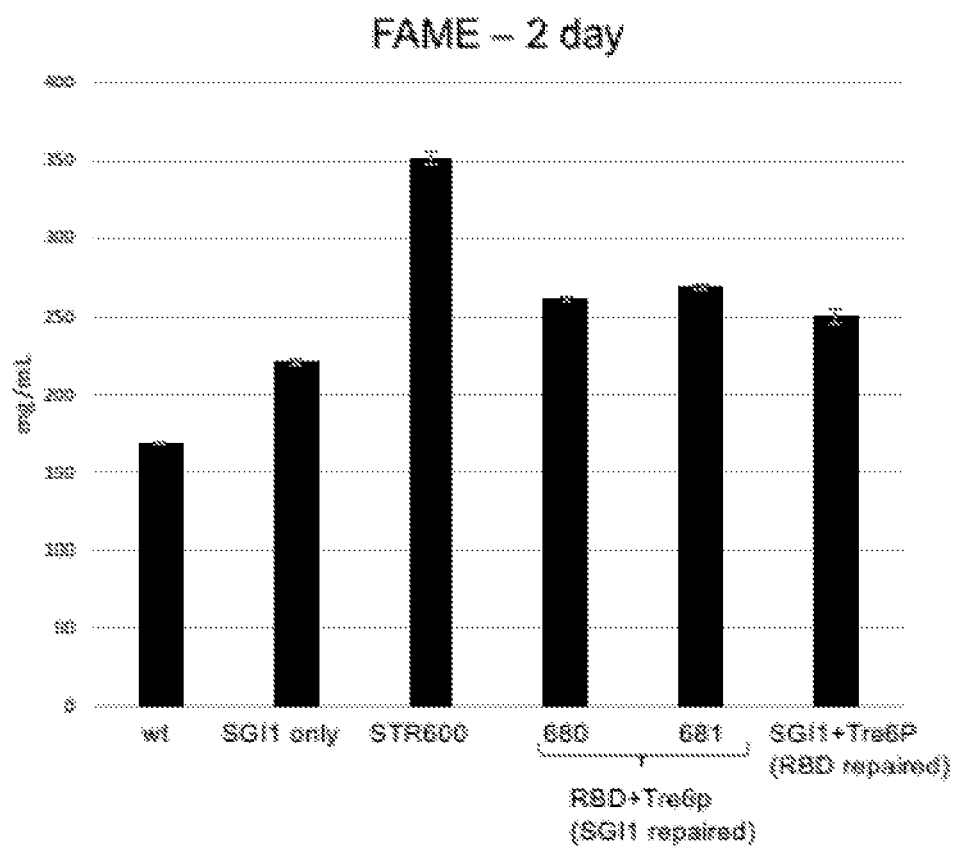
FIGS. 5A-5B shows mutation repair strains versus SGI1-only as background strain.
Figure 5B:
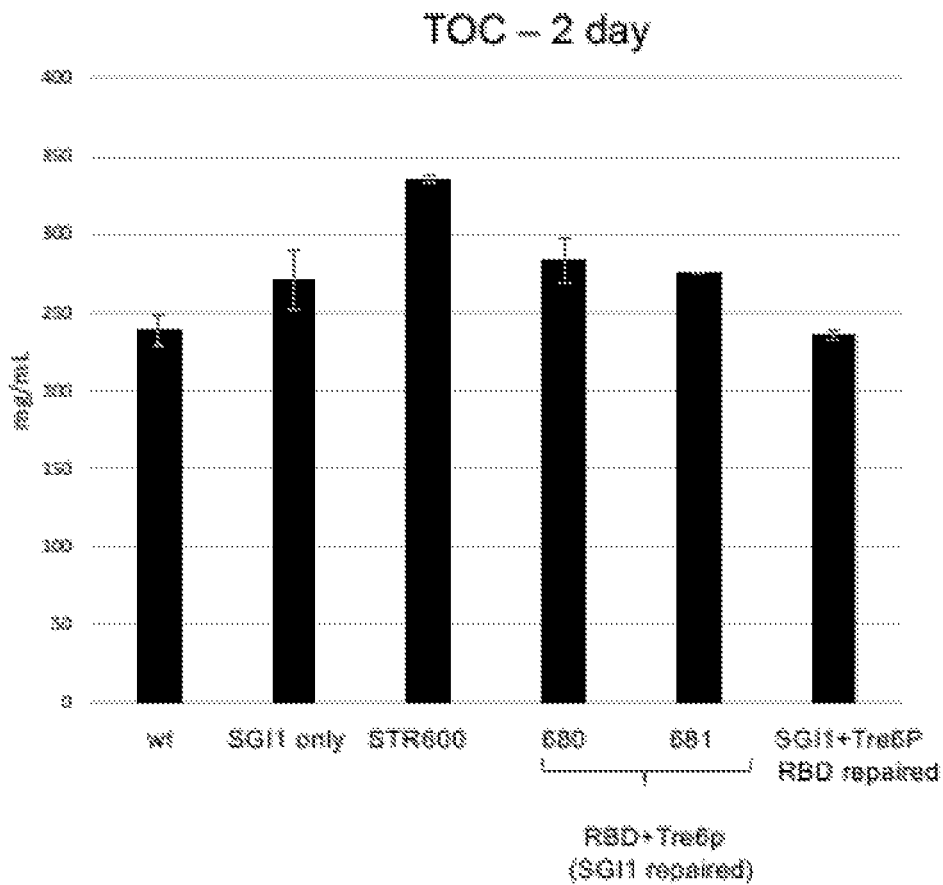

Two mutations were identified as giving rise to the high lipid phenotype. The mutations identified were a Glu723Val (E723V) mutation in the encoded Tre6P enzyme (SEQ ID NO: 2), and a Lys36Stop (Lys36*) mutation in the encoded RBD (SEQ ID NO: 1). It was observed that 1) introducing the Tre6P SNP into a SGI1-KO mutant to produce a mutant having the SGI1-KO+Tre6P attenuation provided a strain with increased lipid productivity, as shown in FIG. 2a; 2) repair of the RBD attenuation to wild-type in Strain 600 (SGI1+RBD+Tre6P) to produce a strain having the SGI1+Tre6P attenuation, resulted in a strain having a decreased lipid productivity (FIG. 2b); 3) introducing the RBD attenuation into the SGI1-only mutant strain resulted in increased lipid productivity under nitrogen deplete batch growth, as shown in FIG. 3a; 4) Tre6P repair in the SGI1+Tre6P+RBD (STR0600) strain resulted in a reduced —N batch lipid productivity, as shown in FIG. 3b, but was still higher than the wild type strain (STR0010) and reached almost as high as the STR0600 having all three modifications; 5) repair of the SGI1 mutation in STR00600 resulted in a reduced —N (nitrogen deplete) batch lipid productivity and TOC productivity, as shown in FIGS. 5a and 5b. FIG. 2c also shows significantly higher FAME productivity for the SGI1+ Tre6P+RBD mutant strain (STR0600) under batch conditions.

Figure 4A:
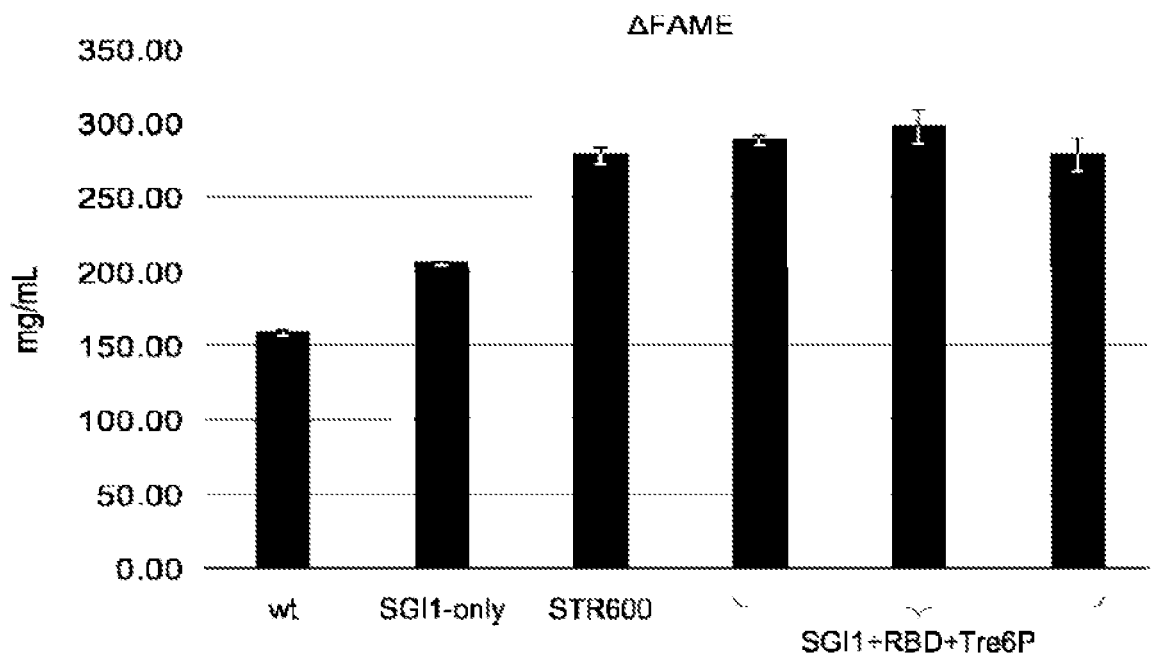
FIGS. 4A-4B shows assay data for RBD and Tre6P mutations stacked into an SGI1 only strain. The data represent the average and standard deviation for biological duplicate cultures, where FAME and TOC productivities are determined over the first two days under nitrogen deplete conditions.
Figure 4B:
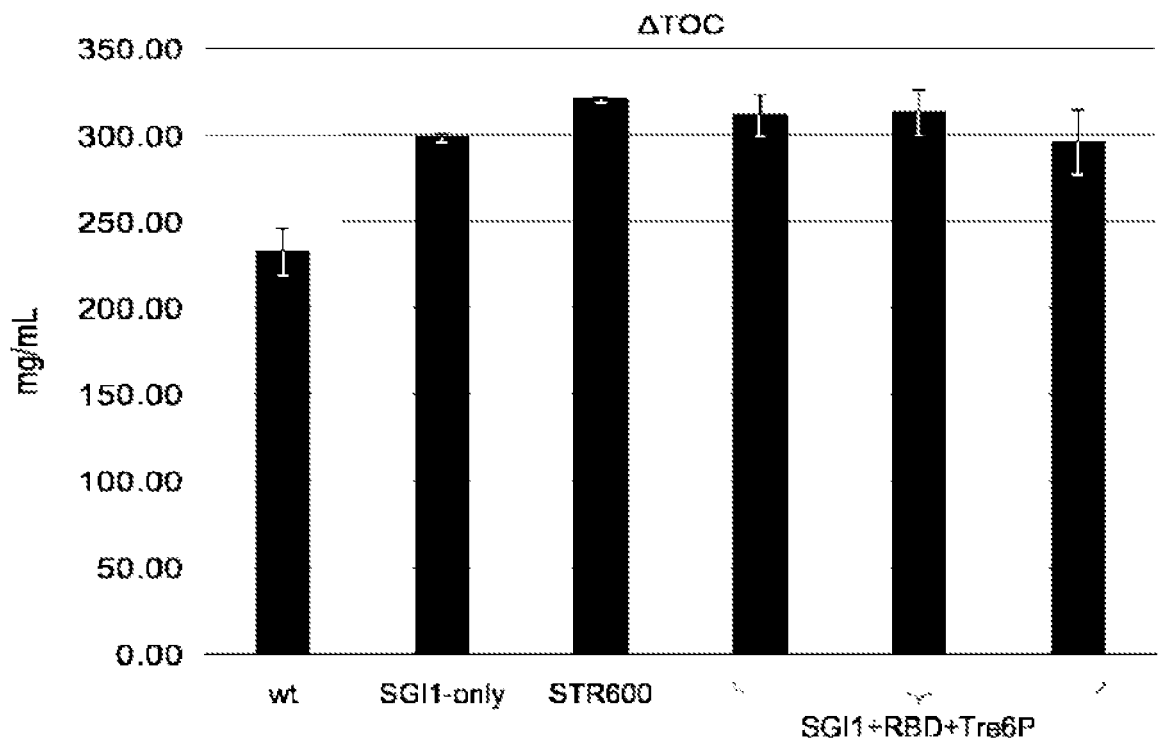

As noted, the strain designated STR0600 has all three genetic modifications, 1) the SGI1 mutation, 2) the RBD mutation, and 3) Tre6P mutations. FIGS. 4a-4b show that the SGI1-only mutant (STR012) exhibited an approximately 30% higher FAME production and TOC production versus the wild-type. FIGS. 4a-4b also show three independent lines that were generated having the SGI1 mutation as well as the RBD and Tre6P attenuations—all three lines showed a lipid productivity and TOC equivalent to STR0600. FIGS. 5a and 5b show two strains (680, 681) having only the RBD and Tre6P mutations, and one having only the SGI1 and Tre6P mutations—these strains showed greater FAME accumulation at Day 2 (55%, 59%, and 49% for FAME, respectively) than wild-type (STR010). The strains also showed 19%, 15% higher TOC accumulation than wild-type for 2-day TOC accumulation). RBD repair resulted in a drop in lipid productivity to a level below the STR0600 and similar to that of the 680 and 681 (RBD+Tre6p) strains.

Therefore, it was shown that the RBD and Tre6P mutations can be "stacked" in an SGI1 mutation strain to recapitulate the high lipid phenotype of STR0600, and the mutations giving rise to the phenotype resolved.

Example 7

Mutation Identification

The genomes of the organisms were sequenced and amino acid sequences of the encoded RBD and Tre6P polypeptides were determined to be SEQ ID NO: 1 and SEQ ID NO: 2, respectively, from the *Parachlorella* sp. Analyses of functional annotation and orthologs present in other organisms revealed that the gene encoding the RNA binding domain protein (SEQ ID NO: 1) has two RNA Recognition Motif (RRM) domains in the N-terminal half of the coding sequence. BLAST searching revealed that orthologs are broadly distributed in green algae with about 50% sequence identity and about 75% positive amino acid identity within amino acid chemical classes (aliphatic, hydroxyl or sulfur-containing, cyclic, aromatic, basic, and acidic and their amide) with the RRM domain observed in maize. The Musashi-like proteins of this class are well characterized RBD proteins (J Cell Sci. 2002 Apr. 1; 115(Pt 7):1355-9), and the function of this class of proteins is believed to be the targeted regulation of translation of mRNAs, and the encoded RNA binding domains in the present case may therefore have similar or the same function.

Figure 6:
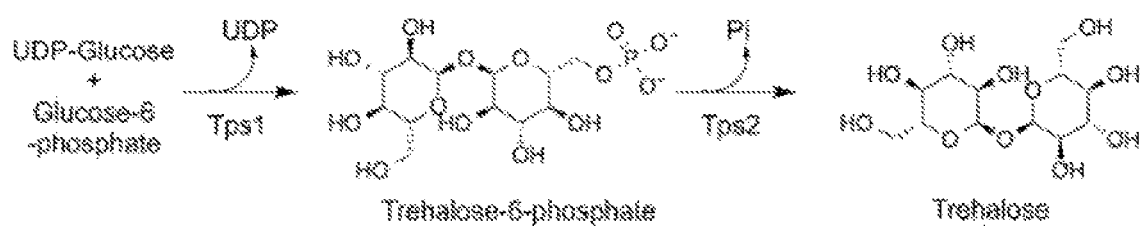
FIG. 6 provides a graphical illustration of a biosynthetic pathway from the conversion of glucose-6-phosphate and UDP-glucose into trehalose-6-phosphate and then trehalose.

SEQ ID NO: 2 is the sequence of a trehalose-6-phosphate synthase/phosphatase from *Parachlorella* sp. that could catalyze reactions analogous to both the Tsp1 and Tsp2 reactions of *Candida albicans*, presented as an example in FIG. 6. The Glu723 was found to be well conserved in homologues as Glu or, in some cases, aspartic acid. Nevertheless, in the recombinant alga of the invention it was found to have mutated to valine and was found to be an E723V mutation.

Although the invention has been described with reference to the above examples, it will be understood that modifications and variations are encompassed within the spirit and scope of the invention. Accordingly, the invention is limited only by the following claims.

What is claimed is:

1. A method of producing a composition containing lipids comprising:
   cultivating a recombinant Chlorophyte algal organism comprising a disruption in a nucleic acid sequence encoding an RNA binding domain having at least 90% sequence identity to SEQ ID NO: 1, wherein the recombinant Chlorophyte alga exhibits increased lipid productivity versus a corresponding control algal cell not having the disruption; and
   thereby producing a composition containing lipids.

2. The method of claim 1 wherein the recombinant Chlorophyte algal organism further comprises a disruption in a nucleic acid sequence encoding an Significant Growth Improvement 1 (SGI1) polypeptide having at least 90% sequence identity to SEQ ID NO: 8.

3. The method of claim 2 wherein the recombinant Chlorophyte alga has at least 5 grams per square meter per day of lipid production.

4. The method of claim 2, wherein the recombinant Chlorophyte alga has higher biomass productivity per unit time versus a corresponding control algal cell not having the disruption.

5. The method of claim 2 wherein the recombinant alga has higher total organic carbon production when cultivated under nitrogen deplete conditions.

6. The method of claim 2 wherein the recombinant alga is a Chlorophyte alga of a genus selected from the group consisting of: *Chorella, Parachlorella, Picochlorum, Tetraselmis*, and *Oocystis*.

7. The method of claim 1 further comprising a step of treating the recombinant Chlorophyte algal organism with ultraviolet radiation prior to the step of cultivating.

8. The method of claim 1 further comprising harvesting a lipidic composition from the recombinant Chlorophyte algal organism.

9. The method of claim 1 wherein the recombinant Chlorophyte algal cell is an alga of the genus *Parachlorella*.

10. The method of claim 9, wherein the recombinant Chlorophyte alga has higher biomass productivity when cultivated under nitrogen deplete conditions.

11. The method of claim 1 wherein the recombinant Chlorophyte alga has at least 50% greater lipid productivity versus the control alga.

12. The method of claim 1, wherein the recombinant Chlorophyte alga is of the Class Trebouxiophyceae.

* * * * *